US010227348B2

(12) United States Patent
Maisch et al.

(10) Patent No.: US 10,227,348 B2
(45) Date of Patent: *Mar. 12, 2019

(54) USE OF 10H-BENZO[G]PTERIDINE-2,4-DIONE DERIVATIVES

(71) Applicant: TriOptoTec GmbH, Regensburg (DE)

(72) Inventors: Tim Maisch, Nürnberg (DE); Andreas Späth, Regensburg (DE)

(73) Assignee: TRIOPTOTEC GMBH (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/653,663

(22) Filed: Jul. 19, 2017

(65) Prior Publication Data

US 2018/0009812 A1  Jan. 11, 2018

Related U.S. Application Data

(63) Continuation of application No. 14/127,453, filed as application No. PCT/EP2012/062142 on Jun. 22, 2012, now Pat. No. 9,796,715.

(30) Foreign Application Priority Data

Jun. 22, 2011  (DE) .................. 10 2011 105 660

(51) Int. Cl.
C07D 475/14 (2006.01)
A01N 43/90 (2006.01)
A61K 31/525 (2006.01)
A61L 15/46 (2006.01)
A61K 41/00 (2006.01)
A61L 29/08 (2006.01)

(52) U.S. Cl.
CPC ........... *C07D 475/14* (2013.01); *A01N 43/90* (2013.01); *A61K 31/525* (2013.01); *A61K 41/0057* (2013.01); *A61L 15/46* (2013.01); *A61L 29/085* (2013.01); *A61L 2300/204* (2013.01)

(58) Field of Classification Search
CPC .... C07D 475/14; A01N 43/90; A61K 31/525; A61K 41/0057; A61L 15/46; A61L 29/085; A61L 2300/204
See application file for complete search history.

(56) References Cited

FOREIGN PATENT DOCUMENTS

| WO | WO 03/057253 A1 | 7/2003 |
| WO | WO 2010/019208 A1 | 2/2010 |
| WO | WO 2011/008247 A1 | 1/2011 |
| WO | WO 2011/126567 A1 | 10/2011 |

OTHER PUBLICATIONS

International Search Report and Written Opinion in German dated Aug. 9, 2012 issued in corresponding International patent application No. PCT/EP2012/062142.

Alexander Barthel, et al., "Synthesis of Dimeric Quinazolin-2-one, 1,4-Benzodiazepin-2-one, and Isoalloxazine Compounds as Inhibitors of Amyloid Peptides Association," Arch. Pharm. Chem. Life Sci., vol. 342, 2009, pp. 445-452.
Michael C. Falk, et al., "Synthetic Flavinyl Peptides Related to the Active Site of Mitochondrial Monoamine Oxidase. I. Chemical and Spectral Properties," Biochemistry, vol. 15, No. 3, 1976, pp. 639-645.
Jens Butenandt, et al., "A Comparative Repair Study of Thymine- and Uracil-Photodimers With Model Compounds and a Photolyase Repair Enzyme," Chem. Eur. J., vol. 6, No. 1, 2000, pp. 62-72.
Carolina Moura, et al., "Rhenium(v) Oxocomplexes With Novel Pyrazolyl-Based $N_4$- and $N_3S$-Donor Chelators," Dalton Transactions, 2006, pp. 5630-5640.
Marcin Jasiński, "Synthesis of New Bis-imidazole Derivatives," Helvetica Chimica Acta, vol. 90, 2007, pp. 1765-1780.
A. A. Miles, et al., "The Estimation of the Bactericidal Power of the Blood," The Journal of Hygiene, vol. 38, No. 6, Nov. 1938, pp. 732-749.
Richard R. Holmes, et al., "A Simple Method for the Direct Oxidation of Aromatic Amines to Nitroso Compounds," vol. 82, 1960, pp. 3454-3456.
Robert Epple, et al., "Investigation of Flavin-Containing DNA-Repair Model Compounds," J. Am. Chem. Soc., vol. 119, 1997, pp. 7440-7451.
Naomi Sakai, et al., "Electrostatics of Cell Membrane Recognition: Structure and Activity of Neutral and Cationic Rigid Push-Pull Rods in Isoelectric, Anionic, and Polarized Lipid Bilayer Membranes," J. Am. Chem. Soc., vol. 123, 2001, pp. 2517-2524.
Sathya Srinivasachari, et al., "Polycationic β-Cyclodextrin 'Click Clusters'": Monodisperse and Versatile Scaffolds for Nucleic Acid Delivery, J. Am. Chem. Soc., vol. 130, pp. 4618-4627.
Youli Xiao, et al., "Revisiting the IspH Catalytic System in the Deoxyxylulose Phosphate Pathway: Achieving High Activity," J. Am. Chem. Soc., vol. 131, 2009, pp. 9931-9933.
Antonio Monge, et al., "Hypoxia-Selective Agents Derived From Quinoxaline 1,4-Di-N-Oxides," J. Med. Chem., vol. 38, 1995, pp. 1786-1792.
Olaf Wiest, et al., "Design, Synthesis, and Evaluation of a Biomimetic Artificial Photolyase Model," J. Org. Chem., vol. 69, 2004, pp. 8183-8185.
Toru Sugaya, et al., "Improved Synthesis of Thromboxane $A_2$ Receptor Antagonists With a Dibenzoxepin Ring System," Synthesis, Oct. 1995, pp. 1257-1262.
Donald B. McCormick, "Flavin Derivatives via Bromination of the 8-Methyl Substituent (1)," Apr. 1970, pp. 447-450.
John M. Boyce, et al., "Guideline for Hand Hygiene in Health-Care Settings. Recommendations of the Healthcare Infection Control Practices Advisory Committee and the HICPAC/SHEA/APIC/IDSA Hand Hygiene Task Force", Am. J. Infect. Control, vol. 30, No. 8, 2002, pp. S1-S46.
John M. Boyce, et al., "Guideline for Hand Hygiene in Health-Care Settings: Recommendations of the Healthcare Infection Control Practices Advisory Committee and the HICPAC/SHEA/APIC/IDSA Hand Hygiene Task Force," Infection Control and Hospital. Epidemiology, vol. 23, No. S12, Dec. 2002, pp. S3-S40.

(Continued)

*Primary Examiner* — Timothy R Rozof
(74) *Attorney, Agent, or Firm* — Ostrolenk Faber LLP

(57) ABSTRACT

Use of 10H-benzo[g]pteridine-2,4-dione derivatives as photosensitizers in the inactivation of microorganisms.

10 Claims, 10 Drawing Sheets

(56) References Cited

OTHER PUBLICATIONS

Figure 1:
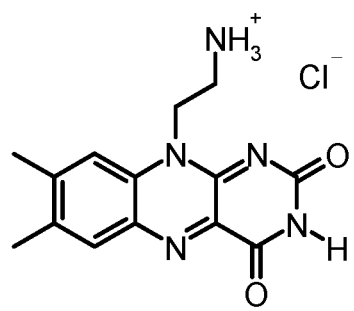

Didier Pittet, MD, et al., "The World Health Organization Guidelines on Hand Hygiene in Health Care and Their Consensus Recommendations," Infection Control and Hospital Epidemiology, vol. 30, No. 7, update from Jul. 2009.

Dr. H. F. Rabenau, et al., ("Leitlinie der Deutschen Vereinigung zur Bekämpfung der Viruskrankheiten (DVV) e.V. und des Robert Koch-Instituts (RKI) zur Prüfung von chemischen Desinfektionsmitteln auf Wirksamkeit gegen Viren in der Humanmedizin" Bundesgesundheitsblatt, Gesundheitsforschung, Gesundheitschutz 51(8), (2008), pp. 937-945) (with English translation)—Guideline of "Deutsche Vereinigung zur Bekämpfung der Viruskrankheiten (DVV; German Association for the Control of Virus Diseases) and Robert Koch Institute (RKI; German Federal Health Authority) for Testing the Virucidal Efficacy of Chemical Disinfectants in the Human Medical Area."

DIN EN 14885:2007-01 "Chemische Desinfektionsmittel und Antiseptika-Anwendung Europäischer Normen für chemische Desinfektionsmittel und Antiseptika;" Deutsche Fassung EN 14885:2006—"Chemical disinfectants and antiseptics—Application of European Standards for chemical disinfectants and antiseptics" (an index in German and English is attached).

Jiri Svoboda, et al., "Thiourea-Enhanced Flavin Photooxidation of Benzyl Alcohol," Chemistry—A European Journal, Feb. 18, 2008, vol. 14, No. 6, pp. 1854-1865.

É. A. Rudzit, et al., "Allo- and Isoalloxazines LI. Synthesis and Antimicrobial Activity of Allo- and Isoalloxazines,"Pharmaceutical Chemistry Journal, Springer New York LLC, US, vol. 12, No. 1, Jan. 1, 1978, pp. 49-54, XP008153978.

Christina K. Remucal, et al., "Photosensitized Amino Acid Degradation in the Presence of Riboflavin and Its Derivatives," Environmental Science & Technology, vol. 45, No. 12, Jun. 15, 2011, pp. 5230-5237, XP55034035.

Nasser K. Thallaj, et al., "The Design of Metal Chelates with a Biologically Related Redox-Active Part: Conjugation of Riboflavin to Bis(2-pyridylmethyl)amine Ligand and Preparation of a Ferric Complex," European Journal of Inorganic Chemistry, vol. 2007, No. 1, Jan. 1, 2007, pp. 44-47, XP55034009.

Michael R. Detty, et al., "Current Clinical and Preclinical Photosensitizers for Use in Photodynamic Therapy," Journal of Medicinal Chemistry, vol. 47, No. 16, Jul. 1, 2004, pp. 3897-3915, XP55034032.

Christopher Cox, et al., "Strong Hydrogen Bonding to the Amide Nitrogen Atom in an "Amide Proton Sponge": Consequences for Structure and Reactivity," Angewandte Chemie, International Edition, Wiley VCH Verlag, Weinheim, vol. 38, No. 6, Jan. 1, 1999, pp. 798-800, XP008154136.

Flavin FL-01:

Flavin Fl-03:

Flavin FL-04:

Flavin FL-05

USE OF 10H-BENZO[G]PTERIDINE-2,4-DIONE DERIVATIVES

The present application is a continuation of prior U.S. patent application Ser. No. 14/127,453, filed Dec. 18, 2013, by Tim Maisch and Andreas Späth, entitled "USE OF 10H-BENZO[G]PTERIDINE-2,4-DIONE DERIVATIVES," which is a 35 U.S.C. § 371 National Phase conversion of PCT/EP2012/062142, filed Jun. 22, 2012, which claims benefit of German Patent Application No. 10 2011 105660.6, filed Jun. 22, 2011. The PCT International Application was published in the German language. The contents of each of the patent applications listed above are incorporated in full herein by reference.

TECHNICAL FIELD OF THE INVENTION

The present invention relates to the use of 10H-benzo[g] pteridine-2,4-dione derivatives.

BACKGROUND OF THE INVENTION

The active or passive penetration of pathogens into a host, the inherent presence of these therein and the propagation thereof is referred to as infection. Sources of infectious particles occur everywhere. For example, the human body is colonized by a large number of microorganisms which are generally kept under control by the normal metabolism and an intact immune system. However, a weakened immune system, for example, may result in significant propagation of the pathogens and, according to the type of pathogen, in different disease symptoms. For many pathogen-induced diseases, medicine has specific antidotes at its disposal, for example antibiotics against bacteria or antimycotics against fungi or virustatics against viruses. However, increasing occurrence of resistant pathogens is observed when these antidotes are used, and some of these pathogens have resistances against several antidotes at the same time. The occurrence of these resistant or multiresistant pathogens has made the treatment of infection disorders increasingly difficult. The clinical consequence of resistance is manifested by a failure of the treatment, particularly in the case of immunosuppressed patients.

New starting points for control of resistant or multi resistant disease pathogens are therefore firstly the search for new antidotes, for example antibiotics or antimycotics, and secondly the search for alternative means of inactivation.

An alternative method which has been found to be useful is the photodynamic inactivation of microorganisms. Two different photooxidative processes play a crucial role in the photodynamic inactivation of microorganisms. Prerequisites for the running of a photooxidative inactivation are firstly the presence of a sufficient amount of oxygen and secondly the localization of a so-called photosensitizer, which is excited by light of an appropriate wavelength. The excited photosensitizer can bring about the formation of reactive oxygen species (ROS), which can form firstly free radicals, for example superoxide anions, hydrogen peroxide or hydroxyl radicals, and/or secondly excited molecular oxygen, for example singlet oxygen.

For both reactions, the photooxidation of specific biomolecules directly adjacent to the reactive oxygen species (ROS) is of primary importance. This involves particularly oxidation of lipids and proteins which occur, for example, as constituents of the cell membrane of microorganisms. The destruction of the cell membrane in turn results in inactivation of the microorganisms in question. For viruses and fungi, a similar elimination process is assumed.

For example, singlet oxygen attacks all molecules. However, unsaturated fatty acids in the membranes of bacteria are particularly prone to damage. Healthy endogenous cells have a cellular defense against attacks by free radicals, called catalases or superoxide dismutases. Therefore, healthy endogenous cells can counteract damage by reactive oxygen species (ROS), for example free radicals or singlet oxygen. The prior art discloses numerous photosensitizers which come, for example, from the group of the porphyrins and derivatives thereof or phthalocyanines and derivatives thereof or fullerenes and derivatives thereof or derivatives of the phenothiazinium structure, for example methylene blue or toluidine blue, or representatives of the phenoxazinium series, for example Nile blue. The photodynamics of methylene blue or toluidine blue with respect to bacteria have already been used, for example, in dentistry.

The photosensitizers known from the prior art are usually substances having a relatively complex molecular structure and therefore complex purification processes.

It is known that 10-methyl-10H-benzo[g]pteridine-2,4-dione derivatives riboflavin and tetraacetylriboflavin have high yields of singlet oxygen, although their affinity for microorganisms is low. It is additionally known that singlet oxygen can diffuse only over a short distance before it reacts or is degraded. Therefore, the inactivation of microorganisms by 10-methyl-10H-benzo[g]pteridine-2,4-dione derivatives riboflavin and tetraacetylriboflavin is inadequate.

Moreover, WO 2010/019208 A1 and WO 2011/008247 A1 disclose numerous flavin, roseoflavin and riboflavin derivatives which can bind to flavin mononucleotide (FMN) riboswitches. Riboswitches are RNA elements in the untranslated regions of the mRNA of prokaryotes, fungi and plants, which bind low molecular weight metabolites, for example FMN, and then regulate gene expression. For example, after binding of FMN to FMN riboswitches of prokaryotes, the expression of enzymes responsible for riboflavin and FMN biosynthesis is repressed, as a result of which riboflavin and FMN biosynthesis stops. Riboflavin assumes a central role in the metabolism, since it serves as a precursor for flavin coenzymes. Therefore, suppressed riboflavin and FMN biosynthesis leads to reduced viability.

However, this form of control of pathogenic microorganisms can likewise result in the occurrence of resistances, which can arise, for example, as a result of mutations in the RNA elements in question.

SUMMARY OF THE INVENTION

It is therefore an object of the present invention to provide novel photosensitizers which more efficiently inactivate microorganisms.

The object of the present invention is achieved by the use of a compound having the formula (1):

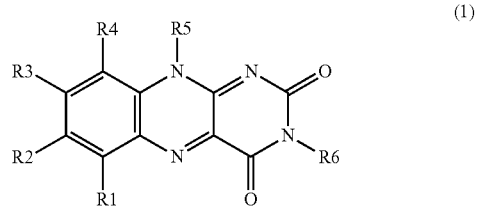

as a photosensitizer in the inactivation of microorganisms, where only 1 R1, R2, R3 or R4 radical is an organic radical of the general formula (2), (3) or (4):

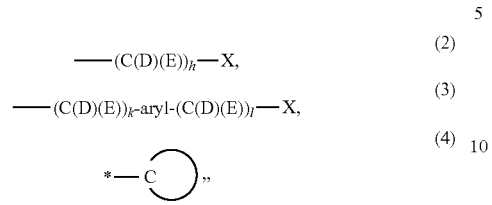

where h is an integer from 1 to 20 and k and l are each independently an integer from 0 to 6, where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, further preferably hydrogen or hydroxyl, and where X is an organic radical having a) only one uncharged, protonatable nitrogen atom, or b) only one positively charged nitrogen atom, which is preferably not a quaternary nitrogen atom, and aryl is a substituted or unsubstituted aromatic system having 5 to 20 carbon atoms or a substituted or unsubstituted heteroaromatic system which does not contain any nitrogen atom and has 4 to 20 carbon atoms, and where the radical having the formula (4) is a heteroaromatic system which is bonded to the isoalloxazine ring via a carbon atom of the heteroaromatic system and which contains a) only one uncharged, protonatable nitrogen atom or b) only one positively charged nitrogen atom, and where the R1, R2, R3 or R4 radicals which are not an organic radical of the general formula (2), (3) or (4) are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl which does not have any nitrogen atom and has 4 to 20 carbon atoms, and where each of the R5 and R6 radicals is the same or different and is independently hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, or where only 1 R5 or R6 radical is an organic radical of the general formula (2), (3) or (4¡:

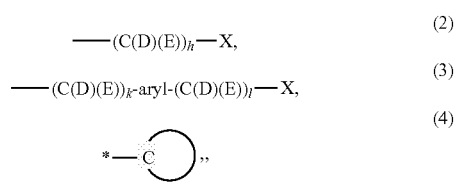

where h is an integer from 1 to 20 and k and l are each independently an integer from 0 to 6, where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, further preferably hydrogen or hydroxyl, and where X is an organic radical having a) only one uncharged, protonatable nitrogen atom, or b) only one positively charged nitrogen atom, which is preferably not a quaternary nitrogen atom, and aryl is a substituted or unsubstituted aromatic system having 5 to 20 carbon atoms or a substituted or unsubstituted heteroaromatic system which does not contain any nitrogen atom and has 4 to 20 carbon atoms, and where the radical having the formula (4) is a heteroaromatic system which is bonded to the isoalloxazine ring via a carbon atom of the heteroaromatic system and which contains a) only one uncharged, protonatable nitrogen atom or b) only one positively charged nitrogen atom, and where the R5 and R6 radical which is not an organic radical of the general formula (2), (3) or (4) is hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, and where the R1 to R4 radicals are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 1 to 20 carbon atoms, S-alkenyl having 1 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 1 to 20 carbon atoms, cycloalkyl having 3 to 20 carbon atoms, cycloalkenyl having 3 to 20 carbon atoms, aryl having 5 to 20 carbon atoms, heteroaryl which does not have any nitrogen atom and has 4 to 20 carbon atoms.

The compound having the formula (1) used in accordance with the invention is a 10H-benzo[g]pteridine-2,4-dione or flavin derivative, which is also referred to as such hereinafter.

The counterion used for the positively charged nitrogen atom may be any suitable anion. Preferably, the counterions used for the positively charged nitrogen atom are anions which enable the provision of a pharmacologically acceptable salt.

DESCRIPTION OF PREFERRED EMBODIMENTS

In a preferred embodiment of the present invention, X in the compound having the formula (1) is an organic radical which has only one positive nitrogen atom which has, as counterion, fluoride, chloride, bromide, iodide, sulfate, hydrogensulfate, phosphate, dihydrogenphosphate, hydrogenphosphate, tosylate, mesylate, formate, acetate, oxalate, benzoate, citrate and/or mixtures thereof.

In a further-preferred embodiment, the X radical is an organic radical containing only one (number=1) basic, preferably uncharged, protonatable, or positively charged, nitrogen atom and no quaternary nitrogen atoms.

Further preferred embodiments of the present invention are described in dependent claims 2 to 11.

According to the invention, "photosensitizer" is understood to mean compounds which absorb electromagnetic radiation, preferably visible light, UV light and/or infrared light, and then generate reactive oxygen species (ROS), preferably free radicals and/or singlet oxygen, from triplet oxygen.

According to the invention, the term "photodynamic therapy" is understood to mean the light-induced inactivation of cells or microorganisms.

According to the invention, the term "inactivation" is understood to mean the reduction of the viability or the destruction of a microorganism, preferably the destruction thereof. A light-induced inactivation can be determined, for example, via reduction in the number of microorganisms after irradiation of a defined starting amount of these microorganisms in the presence of at least one compound having the formula (1) used in accordance with the invention.

According to the invention, a reduction in viability is understood to mean that the number of microorganisms is reduced by at least 99.0%, preferably by at least 99.9%, further preferably by at least 99.99%, further preferably by at least 99.999%, even further preferably by at least 99.9999%. Exceptionally preferably, the number of microorganisms is reduced by more than 99.9 to 100%, preferably by more than 99.99 to 100%.

Preferably, the reduction in the number of microorganisms is reported as the $\log_{10}$ reduction factor according to Boyce, J. M. and Pittet, D. ("Guidelines for hand hygiene in healthcare settings. Recommendations of the Healthcare Infection Control Practices Advisory Committee and the HIPAC/SHEA/APIC/IDSA Hand Hygiene Task Force", Am. J. Infect. Control 30 (8), 2002, pages 1-46).

According to the invention, the term "$\log_{10}$ reduction factor" is understood to mean the difference between the decadic logarithm of the number of microorganisms before and the decadic logarithm of the number of microorganisms after an irradiation of these microorganisms with electromagnetic radiation in the presence of at least one compound having the formula (1) used in accordance with the invention.

Suitable methods for determining the $\log_{10}$ reduction factor are described, for example, in DIN EN 14885:2007-01 "Chemical disinfectants and antiseptics—Application of European Standards for chemical disinfectants and antiseptics" or in Rabenau, H. F. and Schwebke, I. ("Leitlinie der Deutschen Vereinigung zur Bekämpfung der Viruskrankheiten (DVV) e.V. and des Robert Koch-Instituts (RKI) zur Prüfung von chemischen Desinfektionsmitteln auf Wirksamkeit gegen Viren in der Humanmedizin" Bundesgesundheitsblatt, Gesundheitsforschung, Gesundheitsschutz 51(8), (2008), pages 937-945).

Preferably, the $\log_{10}$ reduction factor after irradiation of microorganisms with electromagnetic radiation in the presence of at least one compound having the formula (1) used in accordance with the invention is at least 2 $\log_{10}$, preferably at least 3 $\log_{10}$, further preferably at least 4 $\log_{10}$, further preferably at least 4.5 $\log_{10}$, further preferably at least 5 $\log_{10}$, further preferably at least 6 $\log_{10}$, even further preferably at least 7 $\log_{10}$, even further preferably at least 7.5 $\log_{10}$.

For example, a reduction in the number of microorganisms after irradiation of these microorganisms with electromagnetic radiation in the presence of at least one compound having the formula (1) used in accordance with the invention by 2 orders of magnitude, based on the starting amount of these microorganisms, means a $\log_{10}$ reduction factor of 2 $\log_{10}$.

Further preferably, the number of microorganisms after irradiation of these microorganisms with electromagnetic radiation in the presence of at least one compound having the formula (1) used in accordance with the invention is reduced by at least 1 order of magnitude, further preferably by at least 2 orders of magnitude, preferably by at least 4 orders of magnitude, further preferably by at least 5 orders of magnitude, further preferably by at least 6 orders of magnitude, even further preferably by at least 7 orders of magnitude, based in each case on the starting amount of these microorganisms.

The term "microorganisms" in the context of the invention is understood to mean especially viruses, archaea, prokaryotic microorganisms such as bacteria and bacterial spores, and eukaryotic microorganisms such as fungi, protozoa, fungal spores, unicellular algae. The microorganisms may occur in unicellular or multicellular form, for example as a fungal mycelium.

A 10H-benzo[g]pteridine-2,4-dione derivative used in accordance with the invention in the inactivation of microorganisms has the formula (1)

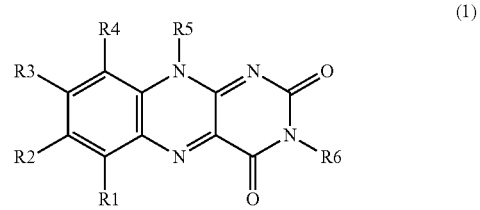

(1)

where either
A) only 1 R1, R2, R3 or R4 radical is an organic radical of the general formula (2), (3) or (4):

(2)

(3)

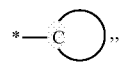

(4)

where h is an integer from 1 to 20, preferably from 1 to 19, preferably from 1 to 17, further preferably from 1 to 13, further preferably from 1 to 9, further preferably from 1 to 6, further preferably from 1 to 4, and k and l are each independently an integer from 0 to 6, preferably from 1 to 5, where D and E are each independently hydrogen, halogen, preferably chlorine, bromine, iodine or fluorine, hydroxyl, O—$R^{(VIII)}$ where $R^{(VIII)}$ is methyl, ethyl, n-propyl, n-butyl, phenyl or benzyl, O—C(=O)—$R^{(IX)}$ where $R^{(IX)}$ is hydrogen, methyl, ethyl, n-propyl, n-butyl, phenyl or benzyl, or thiol, further preferably hydrogen or hydroxyl, and where X is an organic radical having a) only one uncharged, protonatable nitrogen atom, or b) only one positively charged nitrogen atom, which is preferably not a quaternary nitrogen atom, and aryl is a substituted or unsubstituted aromatic system having 5 to 20 carbon atoms or a substituted or unsubstituted heteroaromatic system which does not contain any nitrogen atom and has 4 to 20 carbon atoms, and where the radical having the formula (4) is a heteroaromatic system which is bonded to the isoalloxazine ring via a carbon atom of the heteroaromatic system and which contains a) only one uncharged, protonatable nitrogen atom and/or b) only one positively charged nitrogen atom, or B) only 1 R5 or R6 radical is an organic radical of the general formula (2), (3) or (4):

(2)

(3)

(4)

where h is an integer from 1 to 20, preferably from 1 to 19, preferably from 1 to 17, further preferably from 1 to 13, further preferably from 1 to 9, further preferably from 1 to 6, further preferably from 1 to 4, and k and l are each independently an integer from 0 to 6, preferably from 1 to 5, where D and E are each independently hydrogen, halogen, preferably chlorine, bromine, iodine or fluorine, hydroxyl, O—$R^{(VIII)}$ where $R^{(VIII)}$ is methyl, ethyl, n-propyl, n-butyl, phenyl or benzyl, O—C(=O)—$R^{(IX)}$ where $R^{(IX)}$ is hydrogen, methyl, ethyl, n-propyl, n-butyl, phenyl or benzyl, or thiol, further preferably hydrogen or hydroxyl, and where X is an organic radical having a) only one uncharged, protonatable nitrogen atom, or b) only one positively charged nitrogen atom, which is preferably not a quaternary nitrogen atom, and aryl is a substituted or unsubstituted aromatic system having 5 to 20 carbon atoms or a substituted or unsubstituted heteroaromatic system which does not contain any nitrogen atom and has 4 to 20 carbon atoms, and where the radical having the formula (4) is a heteroaromatic system which is bonded to the isoalloxazine ring via a carbon atom of the heteroaromatic system and which contains a) only one uncharged, protonatable nitrogen atom or b) only one positively charged nitrogen atom.

In a further-preferred embodiment of the 10H-benzo[g]pteridine-2,4-dione derivative of the formula (1) used in accordance with the invention as a photosensitizer in the inactivation of microorganisms, D and E are each hydrogen.

In a preferred embodiment, the 10H-benzo[g]pteridine-2,4-dione derivative of the formula (1) used in accordance with the invention does not have any uncharged, protonatable nitrogen atom bonded directly to the isoalloxazine ring, for example in the form of an amino radical, methylamino radical or dimethylamino radical, or any positively charged nitrogen atom bonded directly to the isoalloxazine ring, for example in the form of a pyridin-1-ium-1-yl radical or trimethylammonio radical.

In a further-preferred embodiment, the 10H-benzo[g]pteridine-2,4-dione derivative of the formula (1) used in accordance with the invention does not contain any further basic, preferably uncharged, protonatable and/or positively charged, nitrogen atoms or any quaternary nitrogen atoms.

In a further preferred embodiment of the 10H-benzo[g]pteridine-2,4-dione derivative of the formula (1) used in accordance with the invention as a photosensitizer in the inactivation of microorganisms, either A) only 1 R1, R2, R3 or R4 radical is an organic radical of the general formula (2), (3) or (4), where h is an integer from 1 to 20, preferably from 1 to 19, preferably from 1 to 17, further preferably from 1 to 13, further preferably from 1 to 9, further preferably from 1 to 6, further preferably from 1 to 4, and k, l are each independently an integer from 0 to 6, preferably from 1 to 5, where D and E are each independently hydrogen, halogen, preferably chlorine, bromine, iodine or fluorine, hydroxyl, O—$R^{(VIII)}$ where $R^{(VIII)}$ is methyl, ethyl, n-propyl, n-butyl, phenyl or benzyl, O—C(=O)—$R^{(IX)}$ where $R^{(IX)}$ is hydrogen, methyl, ethyl, n-propyl, n-butyl, phenyl or benzyl, or thiol, further preferably hydrogen or hydroxyl, and where X is an organic radical having a) only one uncharged, protonatable nitrogen atom, or b) only one positively charged nitrogen atom, which is preferably not a quaternary nitrogen atom, and aryl is a substituted or unsubstituted aromatic system having 5 to 20 carbon atoms or a substituted or unsubstituted heteroaromatic system which does not contain any nitrogen atom and has 4 to 20 carbon atoms, and where the radical having the formula (4) is a heteroaromatic system which is bonded to the isoalloxazine ring via a carbon atom of the heteroaromatic system and which contains a) only one uncharged, protonatable nitrogen atom or b) only one positively charged nitrogen atom, and where the R1, R2, R3 or R4 radicals which are not an organic radical of the general formula (2), (3) or (4) are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl which does not have any nitrogen atom and has 4 to 20 carbon atoms, and where the R5 radical is an acyclic polyol radical of the general formula —$CH_2(CH(OH))_gCH_2OH$ or an ether, ester or acetal thereof, where g is an integer from 1 to 10, preferably 1 to 4, and where R6 is hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, or B) only the R6 radical is an organic radical of the general formula (2), (3) or (4), where h is an integer from 1 to 20, preferably from 1 to 19, preferably from 1 to 17, further preferably from 1 to 13, further preferably from 1 to 9, further preferably from 1 to 6, further preferably from 1 to 4, and k, l are each independently an integer from 0 to 6, preferably from 1 to 5, where D and E are each independently hydrogen, halogen, preferably chlorine, bromine, iodine or fluorine, hydroxyl, O—$R^{(VIII)}$ where $R^{(VIII)}$ is methyl, ethyl, n-propyl, n-butyl, phenyl or benzyl, O—C(=O)—$R^{(IX)}$ where $R^{(IX)}$ is hydrogen, methyl, ethyl, n-propyl, n-butyl, phenyl or benzyl, or thiol, further preferably hydrogen or hydroxyl, and where X is an organic radical having a) only one uncharged, protonatable nitrogen atom, or b) only one positively charged nitrogen atom, which is preferably not a quaternary nitrogen atom, and aryl is a substituted or unsubstituted aromatic system having 5 to 20 carbon atoms or a substituted or unsubstituted heteroaromatic system which does not contain any nitrogen atom and has 4 to 20 carbon atoms, and where the radical having the formula (4) is a heteroaromatic system which is bonded to the isoalloxazine ring via a carbon atom of the heteroaromatic system and which contains a) at least one uncharged, protonatable nitrogen atom or b) at least one positively charged nitrogen atom, and where the R5 radical is an acyclic polyol radical of the general formula —$CH_2(CH(OH))_gCH_2OH$ or an ether, ester or acetal thereof, where g is an integer from 1 to 10, preferably 1 to 4, and where the R1 to R4 radicals are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 1 to 20 carbon atoms, S-alkenyl having 1 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 1 to 20 carbon atoms, cycloalkyl having 3 to 20 carbon atoms, cycloalkenyl having 3 to 20 carbon atoms, aryl having 5 to 20 carbon atoms or heteroaryl which does not have any nitrogen atom and has 4 to 20 carbon atoms.

Further preferably, the R5 radical is an acyclic polyol radical selected from the group consisting of arabityl, ribityl, xylityl, erythrityl, threityl, lactityl, mannityl and sorbityl, further preferably D-ribityl and D-arabityl, or an ether, ester or acetal thereof.

In variant A) of the 10H-benzo[g]pteridine-2,4-dione derivative of the formula (1) used in accordance with the invention as a photosensitizer in the inactivation of microorganisms, only 1 R1, R2, R3 or R4 radical is an organic radical of the general formula (2), (3) or (4), where h is an integer from 1 to 20, preferably from 1 to 19, preferably from 1 to 17, further preferably from 1 to 13, further preferably from 1 to 9, further preferably from 1 to 6, further preferably from 1 to 4, and k, l are each independently an integer from 0 to 6, preferably from 1 to 5, where D and E are each independently hydrogen, halogen, preferably chlorine, bromine, iodine or fluorine, hydroxyl, O—$R^{(VIII)}$ where $R^{(VIII)}$ is methyl, ethyl, n-propyl, n-butyl, phenyl or benzyl, O—C(=O)—$R^{(IX)}$ where $R^{(IX)}$ is hydrogen, methyl, ethyl, n-propyl, n-butyl, phenyl or benzyl, or thiol, further preferably hydrogen or hydroxyl, X is an organic radical having a) only one uncharged, protonatable nitrogen atom, or b) only one positively charged nitrogen atom, which is preferably not a quaternary nitrogen atom, and aryl is a substituted or unsubstituted aromatic system having 5 to 20 carbon atoms or a substituted or unsubstituted heteroaromatic system which does not contain any nitrogen atom and has 4 to 20 carbon atoms, and where the radical having the formula (4) is a heteroaromatic system which is bonded to the isoalloxazine ring via a carbon atom of the heteroaromatic system and which contains a) only one uncharged, protonatable nitrogen atom or b) only one positively charged nitrogen atom, where the R1, R2, R3 or R4 radicals which are an organic radical of the general formula (2), (3) or (4) are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 2 to 20 carbon atoms, O-alkenyl having 1 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl which does not have any nitrogen atom and has 4 to 20 carbon atoms, and where each of the R5 and R6 radicals is the same or different and is independently hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms.

In variant B) of the 10H-benzo[g]pteridine-2,4-dione derivative of the formula (1) used in accordance with the invention as a photosensitizer in the inactivation of microorganisms, only 1 R5 or R6 radical is an organic radical of the general formula (2), (3) or (4), where h is an integer from 1 to 20, preferably from 1 to 19, preferably from 1 to 17, further preferably from 1 to 13, further preferably from 1 to 9, further preferably from 1 to 6, further preferably from 1 to 4, and k, l are each independently an integer from 0 to 6, preferably from 1 to 5, where D and E are each independently hydrogen, halogen, preferably chlorine, bromine, iodine or fluorine, hydroxyl, O—$R^{(VIII)}$ where $R^{(VIII)}$ is methyl, ethyl, n-propyl, n-butyl, phenyl or benzyl, O—C (=O)—R$^{(IX)}$ where R$^{(IX)}$ is hydrogen, methyl, ethyl, n-propyl, n-butyl, phenyl or benzyl, or thiol, further preferably hydrogen or hydroxyl, X is an organic radical having a) only one uncharged, protonatable nitrogen atom, and/or b) only one positively charged nitrogen atom, which is preferably not a quaternary nitrogen atom, and aryl is a substituted or unsubstituted aromatic system having 5 to 20 carbon atoms or a substituted or unsubstituted heteroaromatic system which does not contain any nitrogen atom and has 4 to 20 carbon atoms, and where the radical having the formula (4) is a heteroaromatic system which is bonded to the isoalloxazine ring via a carbon atom of the heteroaromatic system and which contains a) only one uncharged, protonatable nitrogen atom and/or b) only one positively charged nitrogen atom, where the R5 and R6 radical which is not an organic radical of the general formula (2), (3) or (4) is hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, and where the R1 to R4 radicals are the same or different and are each independently hydrogen, halogen, hydroxyl, thiol, nitro, carboxylate, aldehyde having 1 to 20 carbon atoms, ketone having 1 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl which does not have any nitrogen atom and has 4 to 20 carbon atoms.

In a further preferred embodiment of the 10H-benzo[g]pteridine-2,4-dione derivative of the formula (1) used in accordance with the invention as a photosensitizer in the inactivation of microorganisms, either A) only 1 R1, R2, R3 or R4 radical is an organic radical of the general formula (2) or (3):

(2)

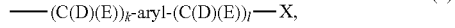

(3)

where h is an integer from 1 to 20, preferably from 1 to 19, preferably from 1 to 17, further preferably from 1 to 13, further preferably from 1 to 9, further preferably from 1 to 6, further preferably from 1 to 4, and k and l are each independently an integer from 0 to 6, preferably from 1 to 5, where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, further preferably hydrogen or hydroxyl, and where X is an organic radical having a) only one uncharged, protonatable nitrogen atom, and/or b) only one positively charged nitrogen atom, which is preferably not a quaternary nitrogen atom, and aryl is a substituted or unsubstituted aromatic system having 5 to 20 carbon atoms or a substituted or unsubstituted heteroaromatic system which does not contain any nitrogen atom and has 4 to 20 carbon atoms, or B) only 1 R5 or R6 radical is an organic radical of the general formula (2) or (3):

(2)

(3)

where h is an integer from 1 to 20, preferably from 1 to 19, preferably from 1 to 17, further preferably from 1 to 13, further preferably from 1 to 9, further preferably from 1 to 6, further preferably from 1 to 4, and k and l are each independently an integer from 0 to 6, preferably from 1 to 5, where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, further preferably hydrogen or hydroxyl, and where X is an organic radical having a) only one uncharged, protonatable nitrogen atom, and/or b) only one positively charged nitrogen atom, which is preferably not a quaternary nitrogen atom, and aryl is a substituted or unsubstituted aromatic system having 5 to 20 carbon atoms or a substituted or unsubstituted heteroaromatic system which does not contain any nitrogen atom and has 4 to 20 carbon atoms.

In a further preferred embodiment of the 10H-benzo[g]pteridine-2,4-dione derivative of the formula (1) used in accordance with the invention as a photosensitizer in the inactivation of microorganisms, either A) only 1 R1, R2, R3 or R4 radical is an organic radical of the general formula (2) or (3), where h is an integer from 1 to 20, preferably from 1 to 19, preferably from 1 to 17, further preferably from 1 to 13, further preferably from 1 to 9, further preferably from 1 to 6, further preferably from 1 to 4, and k, l are each independently an integer from 0 to 6, preferably from 1 to 5, where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, further preferably hydrogen or hydroxyl, and where X is an organic radical having a) only one uncharged, protonatable nitrogen atom, and/or b) only one positively charged nitrogen atom, which is preferably not a quaternary nitrogen atom, and aryl is a substituted or unsubstituted aromatic system having 5 to 20 carbon atoms or a substituted or unsubstituted heteroaromatic system which does not contain any nitrogen atom and has 4 to 20 carbon atoms, where the R1, R2, R3 or R4 radicals which are not an organic radical of the general formula (2) or (3) are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl which does not have any nitrogen atom and has 4 to 20 carbon atoms, and where the R5 radical is an acyclic polyol radical of the general formula —$CH_2(CH(OH))_gCH_2OH$ or an ether, ester or acetal thereof, where g is an integer from 1 to 10, preferably 1 to 4, and where R6 is hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, or B) only the R6 radical is an organic radical of the general formula (2) or (3), where h is an integer from 1 to 20, preferably from 1 to 19, preferably from 1 to 17, further preferably from 1 to 13, further preferably from 1 to 9, further preferably from 1 to 6, further preferably from 1 to 4, and k, l are each independently an integer from 0 to 6, preferably from 1 to 5, where D and E are each independently hydrogen, halogen, preferably chlorine, bromine, iodine or fluorine, hydroxyl, O—$R^{(VIII)}$ where $R^{(VIII)}$ is methyl, ethyl, n-propyl, n-butyl, phenyl or benzyl, O—C(=O)—$R^{(IX)}$ where $R^{(IX)}$ is hydrogen, methyl, ethyl, n-propyl, n-butyl, phenyl or benzyl, or thiol, further preferably hydrogen or hydroxyl, and where X is an organic radical having a) only one uncharged, protonatable nitrogen atom, or b) only one positively charged nitrogen atom, which is preferably not a quaternary nitrogen atom, and aryl is a substituted or unsubstituted aromatic system having 5 to 20 carbon atoms or a substituted or unsubstituted heteroaromatic system which does not contain any nitrogen atom and has 4 to 20 carbon atoms, where the R5 radical is an acyclic polyol radical of the general formula —$CH_2(CH(OH))_gCH_2OH$ or an ether, ester or acetal thereof, where g is an integer from 1 to 10, preferably 1 to 4, and where the R1 to R4 radicals are the same or different and are each independently hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 1 to 20 carbon atoms, S-alkenyl having 1 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 1 to 20 carbon atoms, cycloalkyl having 3 to 20 carbon atoms, cycloalkenyl having 3 to 20 carbon atoms, aryl having 5 to 20 carbon atoms or heteroaryl which does not have any nitrogen atom and has 4 to 20 carbon atoms.

Further preferably, the R5 radical is an acyclic polyol radical selected from the group consisting of arabityl, ribityl, xylityl, erythrityl, threityl, lactityl, mannityl and sorbityl, further preferably D-ribityl and D-arabityl, or an ether, ester or acetal thereof.

In a further preferred embodiment of the 10H-benzo[g]pteridine-2,4-dione derivative of the formula (1) used in accordance with the invention as a photosensitizer in the inactivation of microorganisms, the X radical is a radical of the formula (5):

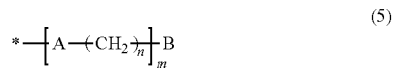

(5)

where A is an oxygen or sulfur atom and where n is an integer from 1 to 8 and m is an integer from 0 to 100, preferably from 0 to 59, preferably from 0 to 10, and where B is a radical of the formula (6a), (6b), (7) or (8):

(6a)

(6b)

(7)

(8)

and where each of the $R^{(I)}$ and $R^{(II)}$ radicals is independently selected from hydrogen and C1-C20 alkyl which may be straight-chain or branched, and where $R^{(III)}$ is hydrogen and where the radical having the formula (8)

(8)

is a substituted or unsubstituted heterocyclic radical having 5 to 7 ring atoms including at least one 1 carbon atom and 1 nitrogen atom and optionally 1 or 2 oxygen or sulfur atoms, where the heterocyclic radical is saturated or unsaturated and preferably does not contain any quaternary nitrogen atoms.

In a further preferred embodiment, the $R^{(I)}$ and $R^{(II)}$ radicals are each independently selected from the group consisting of hydrogen and alkyl groups of the general formula —$(CH_2)_n$—$CH_3$ where n is an integer from 0 to 19, preferably from 1 to 17.

In a further preferred embodiment, the $R^{(I)}$ and $R^{(II)}$ radicals are each independently selected from the group consisting of hydrogen, methyl, ethyl, prop-1-yl, prop-2-yl, but-1-yl, but-2-yl, 2-methylprop-1-yl, 2-methylprop-2-yl, pent-1-yl, pent-2-yl, pent-3-yl, 2-methylbut-1-yl, 2-methylbut-2-yl, 2-methylbut-3-yl, 2-methylbut-4-yl, 2,2-dimethylprop-1-yl, hex-1-yl, hex-2-yl, hex-3-yl, hept-1-yl, oct-1-yl, 2-methylpent-1-yl, 2-methylpent-2-yl, 2-methylpent-3-yl, 2-methylpent-4-yl, 2-methylpent-5-yl, 3-methylpent-1-yl, 3-methylpent-2-yl, 3-methylpent-3-yl, 2,2-dimethylbut-1-yl, 2,2-dimethylbut-3-yl, 2,2-dimethylbut-4-yl, 2,3-dimethylbut-1-yl and 2,3-dimethylbut-2-yl. In a particularly preferred embodiment, the $R^{(I)}$, $R^{(II)}$ and $R^{(III)}$ radicals are each independently selected from the group consisting of methyl, ethyl, prop-1-yl, but-1-yl, pent-1-yl, hex-1-yl, hept-1- and oct-1-yl.

In a further preferred embodiment, the $R^{(I)}$ and $R^{(II)}$ radicals are each independently hydrogen or the radical having the formula (11):

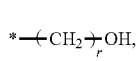

(11)

where r is an integer from 1 to 20, preferably from 1 to 8, further preferably from 1 to 4.

In a further preferred embodiment, the radical of the formula (4):

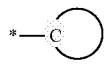

(4)

is selected from the group consisting of radicals of the formulae (13a), (13b) and (13c)

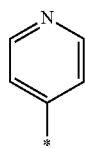

(13a)

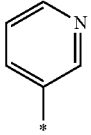

(13b)

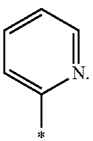

(13c)

In a further preferred embodiment, the radical having the formula (8):

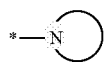

(8)

is a substituted or unsubstituted heterocyclic radical having 5 to 7 ring atoms including at least one 1 carbon atom and 1 nitrogen atom and optionally 1 or 2 oxygen or sulfur atoms, where the heterocyclic radical is saturated or unsaturated and preferably does not contain any quaternary nitrogen atoms.

According to the invention, the term "heterocyclic" is understood to mean cyclic compounds having ring-forming atoms of at least two different chemical elements, preferably carbon, nitrogen, oxygen or sulfur.

In a further preferred embodiment, the radical having the formula (4) is selected from the group consisting of azolyls, azolinyls, azolidinyls, thiazolyls, oxazolyls, oxazolinyls, oxazolidinyls, oxazinyls, dihydrooxazinyls, tetrahydrooxazinyls, thiazinyls, azepanyls, azepinyls and thiaazepinyls, where the aforementioned heterocyclic radicals are unsubstituted or may be substituted by at least one radical selected from the group consisting of halogen, preferably chlorine, bromine, iodine or fluorine, phenyl, benzyl, straight-chain or branched alkyl having 1 to 20 carbon atoms and hydroxyl, and preferably do not contain any quaternary nitrogen atoms.

In a further-preferred embodiment, the radical having the formula (4) is formed from compounds having 5 to 7 ring atoms, these compounds being selected from the group consisting of pyrrolidine, pyrrole, oxazole, oxazoline, oxazolidine, isoxazole, isoxazoline, isoxazolidine, thiazole, thiazoline, thiazolidine, isothiazole, isothiazoline, isothiazolidine, piperidine, pyridine, oxazines, dihydrooxazines, tetrahydrooxazines, preferably morpholine, thiazine, azepines, azepane, and thiazepines, where the aforementioned compounds are unsubstituted or may be substituted by at least one radical selected from the group consisting of halogen, preferably chlorine, bromine, iodine or fluorine, phenyl, benzyl, straight-chain or branched alkyl having 1 to 20 carbon atoms and hydroxyl, and preferably do not contain any quaternary nitrogen atoms.

In a particularly preferred embodiment, the radical of the formula (4) is selected from the group which of pyrrolidinyl, piperidinyl, morpholinyl, pyridinyl, aminopyridinyl, azepan-1-yl, 2,3,4,5-tetrahydro-1-benzazepin-1-yl, 2,3,4,5-tetrahydro-3-benzazepin-3-yl.

In a further preferred embodiment, the radical having the formula (8):

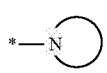

(8)

is a substituted or unsubstituted cyclic heteroalkyl radical having 5 to 7 ring atoms including at least one 1 carbon atom and 1 nitrogen atom and optionally 1 or 2 oxygen or sulfur atoms and preferably no quaternary nitrogen atoms, or a substituted or unsubstituted cyclic heteroalkenyl radical having 5 to 7 ring atoms including at least one 1 carbon atom and 1 nitrogen atom and optionally 1 or 2 oxygen or sulfur atoms, and preferably no quaternary nitrogen atoms.

In variant A) and variant B) of the 10H-benzo[g]pteridine-2,4-dione derivative of the formula (1) used in accordance with the invention as a photosensitizer in the inactivation of microorganisms, aforementioned aldehyde radicals, ketone radicals, carboxylic acid radicals, carboxamide radicals, thioester radicals, cycloalkyl radicals, cycloalkenyl radicals, alkyl radicals and alkenyl radicals may be straight-chain or branched, preferably straight-chain, and either be unsubstituted or substituted by at least one radical selected from the group consisting of hydroxyl, halogen, preferably chlorine, bromine, iodine or fluorine, thiol, nitro, ester, ether and acetal.

In a further preferred embodiment, the aforementioned alkyl radicals are each selected from the group consisting of methyl, ethyl, n-propyl, n-butyl, n-pentyl, n-hexyl, n-heptyl and n-octyl.

In a further-preferred embodiment, the aforementioned alkyl radicals may be acyclic polyol radicals of the general formula —$CH_2(CH(OH))_gCH_2OH$ where g is an integer from 1 to 10, preferably 1 to 4. Further preferably, the acyclic polyol radicals are selected from the group consisting of arabityl, ribityl, xylityl, erythrityl, threityl, lactityl, mannityl and sorbityl, further preferably D-ribityl and D-arabityl.

In a preferred embodiment of the 10H-benzo[g]pteridine-2,4-dione derivative of the formula (1) used in accordance with the invention as a photosensitizer in the inactivation of microorganisms, the aryl radicals each have not more than 4, further preferably not more than 3, further preferably not more than 2, fused rings. Even further preferably, the aryl radicals each have 1 ring.

In a preferred embodiment of the 10H-benzo[g]pteridine-2,4-dione derivative of the formula (1) used in accordance with the invention as a photosensitizer in the inactivation of microorganisms, the aforementioned aryl radicals are selected from the group consisting of phenyl, benzyl, naphthyl, anthracenyl, phenanthenyl and pyrenyl.

In a preferred embodiment of the 10H-benzo[g]pteridine-2,4-dione derivative of the formula (1) used in accordance with the invention as a photosensitizer in the inactivation of microorganisms, the aforementioned alkenyl radicals have 2 to 17 carbon atoms, further preferably 2 to 13 carbon atoms, further preferably 2 to 9 carbon atoms, further preferably 2 to 5 carbon atoms. In a further-preferred embodiment, the aforementioned alkenyl radicals are selected from the group consisting of ethenyl, n-propenyl and n-butenyl.

In a further preferred embodiment of the 10H-benzo[g]pteridine-2,4-dione derivative of the formula (1) used in accordance with the invention as a photosensitizer in the inactivation of microorganisms, the aforementioned aldehydes have 1 to 17 carbon atoms, further preferably 1 to 13 carbon atoms, further preferably 1 to 9 carbon atoms, further preferably 1 to 5 carbon atoms. In a further-preferred embodiment, the aforementioned aldehydes are selected from the group consisting of methanal-1-yl (formyl), ethanal-1-yl (2-oxoethyl), n-propanal-1-yl (3-oxopropyl) and n-butanal-1-yl (4-oxobutyl).

In a further preferred embodiment of the 10H-benzo[g]pteridine-2,4-dione derivative of the formula (1) used in accordance with the invention as a photosensitizer in the inactivation of microorganisms, the aforementioned ketones have 2 to 17 carbon atoms, further preferably 3 to 14 carbon atoms, further preferably 3 to 9 carbon atoms. In a further-preferred embodiment, the aforementioned ketones are selected from the group consisting of dimethyl ketyl, methyl ethyl ketyl, ethyl methyl ketyl, diethyl ketyl, methyl propyl ketyl, ethyl propyl ketyl, propyl methyl ketyl, propyl ethyl ketyl and dipropyl ketyl, which may be straight-chain or branched.

In a further-preferred embodiment, the aforementioned aldehyde radicals and/or ketone radicals may be monosaccharide radicals, preferably pentose or ketose radicals.

Preferably, suitable monosaccharide radicals have 3 to 7 carbon atoms, preferably 5 to 6 carbon atoms, and have one carbonyl group, preferably aldehyde group or keto group, and at least one hydroxyl group and may be open-chain or cyclic, preferably in the form of furanose or pyranose.

Preferably, suitable monosaccharide radicals derive from monosaccharides selected from the group consisting of D-glyceraldehyde, L-glyceraldehyde, D-erythrose, L-erythrose, D-threose, L-threose, D-ribose, L-ribose, D-arabinose, L-arabinose, D-xylose, L-xylose, D-lyxose, L-lyxose, D-allose, L-allose, D-altrose, L-altrose, D-glucose, L-glucose, D-mannose, L-mannose, D-gulose, L-gulose, D-idose, L-idose, D-galactose, L-galactose, D-talose, L-talose, dihydroxyacetone, D-erythrulose, L-erythrulose, D-ribulose, L-ribulose, D-xylulose, L-xylulose, D-psicose, L-psicose, D-fructose, L-fructose, D-sorbose, L-sorbose, D-tagatose and L-tagatose. Further preferably, suitable monosaccharides are selected from the group consisting of D-ribose, L-ribose, D-arabinose, L-arabinose, D-xylose, L-xylose, D-lyxose, L-lyxose, D-allose, L-allose, D-altrose, L-altrose, D-glucose, L-glucose, D-mannose, L-mannose, D-gulose, L-gulose, D-idose, L-idose, D-galactose, L-galactose, D-talose, L-talose, D-ribulose, L-ribulose, D-xylulose, L-xylulose, D-psicose, L-psicose, D-fructose, L-fructose, D-sorbose, L-sorbose, D-tagatose and L-tagatose.

In a further preferred embodiment of the 10H-benzo[g]pteridine-2,4-dione derivative of the formula (1) used in accordance with the invention as a photosensitizer in the inactivation of microorganisms, the aforementioned carboxylic esters have 1 to 17 carbon atoms, further preferably 1 to 15 carbon atoms, further preferably 1 to 12 carbon atoms. In a further-preferred embodiment, the aforementioned carboxylic esters are selected from the group consisting of ethyl esters, n-propyl esters, i-propyl esters, n-butyl esters, sec-butyl esters, tert-butyl esters and benzyl esters.

In a further preferred embodiment of the 10H-benzo[g]pteridine-2,4-dione derivative of the formula (1) used in accordance with the invention as a photosensitizer in the inactivation of microorganisms, the aforementioned carboxamides have 1 to 17 carbon atoms, further preferably 1 to 15 carbon atoms, further preferably 1 to 12 carbon atoms. In a further-preferred embodiment, the aforementioned carboxamides are selected from the group consisting of amide, N-methylamide, N-ethylamide, N-(n-propyl)amide, N-(i-propyl)amide, N-(n-butyl)amide, N-(sec-butyl)amide, N-(tert-butyl)amide, N-phenylamide, N-benzylamide, N,N-dimethylamide, N-methyl-N-ethylamide, N,N-diethylamide, N-methyl-N-(n-propyl)amide, N-methyl-N-(i-propyl)amide, N-methyl-N-(n-butyl)amide, N-methyl-N-(sec-butyl)amide, N-methyl-N-(tert-butyl)amide, N-ethyl-N-(n-propyl)amide, N-ethyl-N-(i-propyl)amide, N-ethyl-N-(n-butyl)amide, N-ethyl-N-(sec-butyl)amide, N-ethyl-N-(tert-butyl)amide, N-(n-propyl)-N-(n-propyl)amide, N-(n-propyl)-N-(i-propyl)amide, N-(n-propyl)-N-(n-butyl)amide, N-(n-propyl)-N-(sec-butyl)amide, N-(n-propyl)-N-(tert-butyl)amide, N-(i-propyl)-N-(n-propyl)amide, N-(i-propyl)-N-(i-propyl)amide, N-(i-propyl)-N-(n-butyl)amide, N-(i-propyl)-N-(sec-butyl)amide, N-(i-propyl)-N-(tert-butyl)amide, N-(n-butyl)-N-(n-propyl)amide, N-(n-butyl)-N-(i-propyl)amide, N-(n-butyl)-N-(n-butyl)amide, N-(n-butyl)-N-(sec-butyl)amide, N-(n-butyl)-N-(tert-butyl)amide, N-(sec-butyl)-N-(n-propyl)amide, N-(sec-butyl)-N-(i-propyl)amide, N-(sec-butyl)-N-(n-butyl)amide, N-(sec-butyl)-N-(sec-butyl)amide, N-(sec-butyl)-N-(tert-butyl)amide, N-(tert-butyl)-N-(n-propyl)amide, N-(tert-butyl)-N-(i-propyl)amide, N-(tert-butyl)-N-(n-butyl)amide, N-(tert-butyl)-N-(sec-butyl)amide, N-(tert-butyl)-N-(tert-butyl)amide, N,N-diphenylamide, N,N-dibenzylamide, N-phenyl-N-benzylamide, N-methyl-N-phenylamide, N-methyl-N-benzylamide, N-ethyl-N-phenylamide, N-ethyl-N-benzylamide, N-phenyl-N-(n-propyl)amide, N-phenyl-N-(i-propyl)amide, N-phenyl-N-(n-butyl)amide, N-phenyl-N-(sec-butyl)amide, N-phenyl-N-(tert-butyl)amide, N-benzyl-N-(n-propyl) amide, N-benzyl-N-(i-propyl)amide, N-benzyl-N-(n-butyl) amide, N-benzyl-N-(sec-butyl)amide and N-benzyl-N-(tert-butyl)amide.

In a further preferred embodiment of the 10H-benzo[g] pteridine-2,4-dione derivative of the formula (1) used in accordance with the invention as a photosensitizer in the inactivation of microorganisms, the aforementioned heteroaryl rest which does not contain any nitrogen atom and has 4 to 20 carbon atoms is selected from the group consisting of thiophenyl, furanyl, benzothiofuranyl and benzofuranyl.

In a further preferred embodiment of the 10H-benzo[g] pteridine-2,4-dione derivative of the formula (1) used in accordance with the invention as a photosensitizer in the inactivation of microorganisms, the aforementioned ether radicals have 2 to 17 carbon atoms, further preferably 2 to 13 carbon atoms, further preferably 2 to 9 carbon atoms. In a further-preferred embodiment, the aforementioned ether radicals are selected, for example, from the group consisting of methoxymethyl, methoxyethyl, methoxy-n-propyl, ethoxymethyl, n-propoxymethyl, 2-ethoxyethoxymethyl, 2-(2-ethoxyethoxy)ethyl, i-propoxymethyl, tert-butyloxymethyl and benzyloxymethyl.

In a further preferred embodiment of the 10H-benzo[g] pteridine-2,4-dione derivative of the formula (1) used in accordance with the invention as a photosensitizer in the inactivation of microorganisms, the aforementioned thioether radicals have 2 to 17 carbon atoms, further preferably 2 to 13 carbon atoms, further preferably 2 to 9 carbon atoms. In a further-preferred embodiment, the aforementioned thioether radicals are selected, for example, from the group methylsulfanylmethyl, methylsulfanylethyl, 3-methylsulfanyl-n-propyl, ethylsulfanylmethyl, n-propylsulfanylm ethyl, 2-ethylsulfanylethylsulfanylmethyl, 2-(2-ethylsulfanylethylsulfanyl)ethyl, 2-methylsulfanylpropyl, tert-butylsulfanymethyl and benzylsulfanymethyl consists.

In a further preferred embodiment, the 10H-benzo[g] pteridine-2,4-dione derivative of the formula (1) used in accordance with the invention as a photosensitizer in the inactivation of microorganisms has a molecular weight of less than 1300 g/mol, preferably less than 990 g/mol, further preferably less than 810 g/mol, further preferably less than 690 g/mol, even further preferably less than 610 g/mol, even further preferably less than 600 g/mol, even further preferably less than 570 g/mol.

Chiral centers, unless stated otherwise, may be in the R or S configuration. The invention relates both to the optically pure compounds and to stereoisomer mixtures, such as enantiomer mixtures and diastereomer mixtures, in any ratio.

The invention preferably also relates to the use of mesomers and/or tautomers of the compound having the formula (1), both to the use of the pure compounds and to the use of isomer mixtures in any ratio.

In a further preferred embodiment, the 10H-benzo[g] pteridine-2,4-dione derivative of the formula (1) used in accordance with the invention as a photosensitizer in the inactivation of microorganisms is selected from the group consisting of the compounds having the formulae (14) to (17):

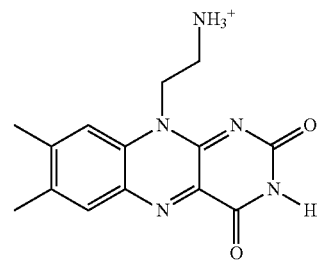
(14)

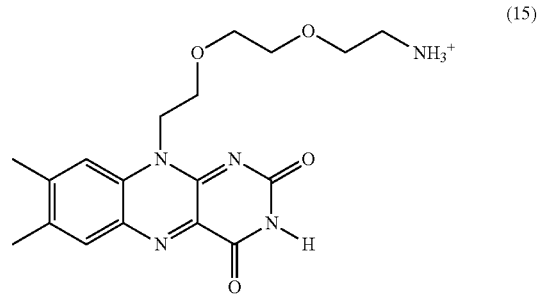
(15)

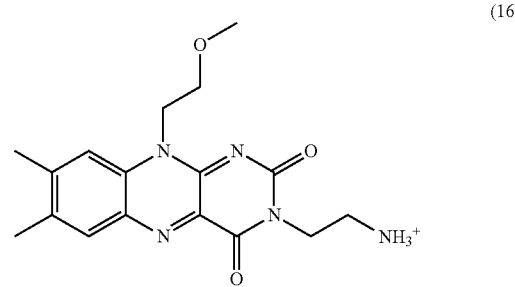
(16)

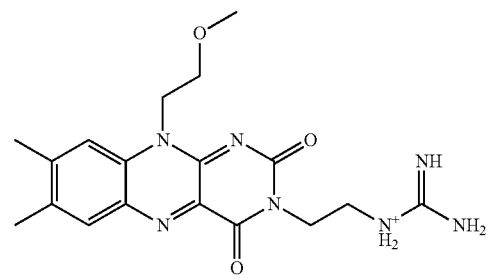
(17)

The 10H-benzo[g]pteridine-2,4-dione derivatives of the formula (1) used in the present application can be prepared, for example, by processes described hereinafter, the process comprising the following steps:

(A) reducing a substituted nitroaniline of the formula (30) to a substituted o-phenylenediamine of the formula (31), preferably by means of hydrogen and palladium on activated carbon or with tin(II) chloride,

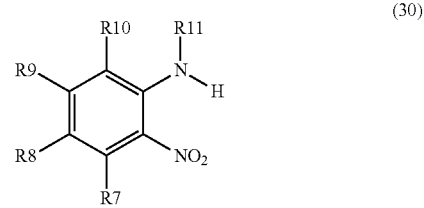
(30)

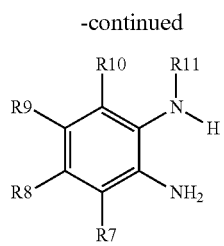

(31)

where each of the R7 to R10 radicals, which may each be independently the same or different, is hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms, heteroaryl having 4 to 20 carbon atoms, which does not contain any nitrogen atoms, or an organic radical of the general formula —(C(D)(E))$_h$-OH, —(C(D)(E))$_k$-aryl-(C(D)(E))$_l$-OH, —(C(D)(E))$_h$-X or —(C(D)(E))$_k$-aryl-(C(D)(E))$_l$-X, and where the R11 radical is hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms, heteroaryl having 4 to 20 carbon atoms, which does not contain any nitrogen atom, or an organic radical of the general formula —(C(D)(E))$_h$-OH or —(C(D)(E))$_k$-aryl-(C(D)(E))$_l$-OH, —(C(D)(E))$_h$-X or —(C(D)(E))$_k$-aryl-(C(D)(E))$_l$-X, (B) condensing the substituted o-phenylenediamine of the formula (31) obtained in step (A) with alloxane or the hydrate thereof to obtain a compound having the formula (32), optionally in the presence of a catalyst, preferably Lewis acid or Brønsted acid, further preferably acetic acid in the presence of boric acid,

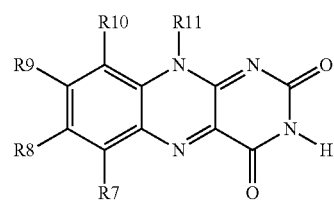

(32)

(C) optionally reacting the compound of the formula (32) obtained in step (B) with an alkylating agent of the general formula T-alkyl, T-alkenyl, T-cycloalkyl, T-cycloalkenyl, T-(C(D)(E))$_h$-OH, T-(C(D)(E))$_k$-aryl-(C(D)(E))$_l$-OH, T-aryl, T-(C(D)(E))$_h$-X or T-(CH$_2$)$_k$-aryl-(C(D)(E))$_l$-X, where the T radical is hydrogen, chlorine, bromine, iodine, p-toluenesulfonyl (OTs), methanesulfonyl (OMs), OH or R$_2$S$^+$, where each R may independently be the same or different and is preferably methyl, ethyl, propyl or butyl, to obtain a compound having the formula (33):

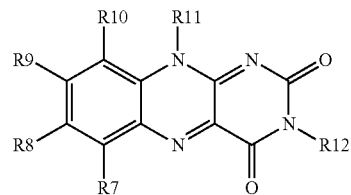

(33)

(D) optionally reacting the compound of the formula (32) obtained in step (B) or the compound of the formula (33) obtained in step (C) with tosyl chloride, mesyl chloride or iodine, optionally in the presence of a catalyst, and subsequently with an organic compound containing at least one tertiary nitrogen atom, when none of the R7 to R12 radicals is an organic radical of the general formula —(C(D)(E))$_h$-X or —(C(D)(E))$_k$-aryl-(C(D)(E))$_l$-X and when 1 R7 to R12 radical is an organic radical of the general formula —(C(D)(E))$_h$-OH or —(C(D)(E))$_k$-aryl-(C(D)(E))$_l$-OH, to obtain the inventive 10H-benzo[g]pteridine-2,4-dione derivative of the formula (1), with the proviso that only 1 R7 to R12 radical is an organic radical of the general formula (2), (3) or (4):

$$—(C(D)(E))_h—X, \quad (2)$$

$$—(C(D)(E))_k\text{-aryl-}(C(D)(E))_l—X, \quad (3)$$

$$,, \quad (4)$$

where h is an integer from 1 to 20 and k and l are each independently an integer from 0 to 6, where D and E are each independently hydrogen, halogen, preferably chlorine, bromine, iodine or fluorine, hydroxyl, O—R$^{(VIII)}$ where R$^{(VIII)}$ is methyl, ethyl, n-propyl, n-butyl, phenyl or benzyl, O—C(=O)—R$^{(IX)}$ where R$^{(IX)}$ is hydrogen, methyl, ethyl, n-propyl, n-butyl, phenyl or benzyl, or thiol, further preferably hydrogen or hydroxyl, and where X is an organic radical having a) only one uncharged, protonatable nitrogen atom, or b) only one positively charged nitrogen atom, which is preferably not a quaternary nitrogen atom, and aryl is a substituted or unsubstituted aromatic system having 5 to 20 carbon atoms or a substituted or unsubstituted heteroaromatic system which does not contain any nitrogen atom and has 4 to 20 carbon atoms, and where the radical having the formula (4) is a heteroaromatic system which is bonded to the isoalloxazine ring via a carbon atom of the heteroaromatic system and which contains a) only one uncharged, protonatable nitrogen atom or b) only one positively charged nitrogen atom.

The 10H-benzo[g]pteridine-2,4-dione derivatives of the formula (1) used in the present application can also be prepared by processes described hereinafter, the process comprising the following steps:

(A) condensing an amine having the formula R11-NH$_2$ with a chlorouracil derivative of the formula (34), optionally in the presence of a catalyst, preferably Lewis acid or Brønsted acid, to obtain a compound having the formula (35):

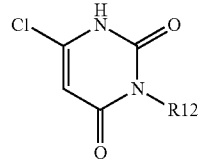

(34)

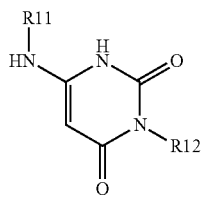

(35)

where each of the R11 and R12 radicals may independently be the same or different and is hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms, heteroaryl having 4 to 20 carbon atoms, which does not contain any nitrogen atom, or an organic radical of the general formula —$(C(D)(E))_h$-OH or —$(C(D)(E))_k$-aryl-$(C(D)(E))_l$-OH, —$(C(D)(E))_h$-X or —$(C(D)(E))_k$-aryl-$(C(D)(E))_l$-X, (B) reacting the compound of the formula (35) obtained in step (A) with a nitroso compound of the formula (36) to obtain a compound of the formula (33):

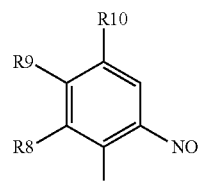

(36)

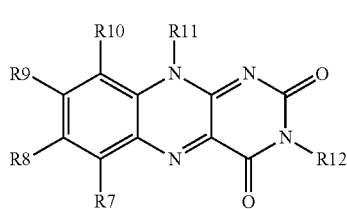

(33)

where each of the R7 to R10 radicals may independently be the same or different and is hydrogen, halogen, hydroxyl, thiol, nitro, carboxylate, aldehyde having 1 to 20 carbon atoms, ketone having 2 to 20 carbon atoms, O-alkyl having 1 to 20 carbon atoms, S-alkyl having 1 to 20 carbon atoms, O-alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 1 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms, heteroaryl having 4 to 20 carbon atoms, which does not contain any nitrogen atoms, or an organic radical of the general formula —$(C(D)(E))_h$-OH, —$(C(D)(E))_k$-aryl-$(C(D)(E))_l$-OH, —$(C(D)(E))_h$-X or —$(C(D)(E))_k$-aryl-$(C(D)(E))_l$-X, and (C) optionally reacting the compound of the formula (33) obtained in step (B) with tosyl chloride, mesyl chloride or iodine, optionally in the presence of a catalyst, and subsequently with an organic compound containing at least one tertiary nitrogen atom, when none of the R7 to R12 radicals is an organic radical of the general formula —$(C(D)(E))_h$-X or —$(C(D)(E))_k$-aryl-$(C(D)(E))_l$-X and when 1 R7 to R12 radical is an organic radical of the general formula —$(C(D)(E))_h$-OH or —$(C(D)(E))_k$-aryl-$(C(D)(E))_l$-OH, to obtain the inventive 10H-benzo[g]pteridine-2,4-dione derivative of the formula (1), with the proviso that only 1 R7 to R12 radical is an organic radical of the general formula (2), (3) or (4), where h is an integer from 1 to 20 and k and l are each independently an integer from 0 to 6, where D and E are each independently hydrogen, halogen, preferably chlorine, bromine, iodine or fluorine, hydroxyl, O—$R^{(VIII)}$ where $R^{(VIII)}$ is methyl, ethyl, n-propyl, n-butyl, phenyl or benzyl, O—C(=O)—$R^{(IX)}$ where $R^{(IX)}$ is hydrogen, methyl, ethyl, n-propyl, n-butyl, phenyl or benzyl, or thiol, further preferably hydrogen or hydroxyl, and where X is an organic radical having a) only one uncharged, protonatable nitrogen atom, or b) only one positively charged nitrogen atom, which is preferably not a quaternary nitrogen atom, and aryl is a substituted or unsubstituted aromatic system having 5 to 20 carbon atoms or a substituted or unsubstituted heteroaromatic system which does not contain any nitrogen atom and has 4 to 20 carbon atoms, and where the radical having the formula (4) is a heteroaromatic system which is bonded to the isoalloxazine ring via a carbon atom of the heteroaromatic system and which contains a) only one uncharged, protonatable nitrogen atom or b) only one positively charged nitrogen atom.

When different amino protecting groups PG are used in a synthesis, there is the option of an orthogonal protecting group strategy, in which case different amino functions in one molecule can be selectively released and reacted in succession.

Suitable methods for removing the amino protecting group PG are known from the prior art. For example, benzyloxycarbonyl (Cbz) can be removed again by catalytic hydrogenation with hydrogenolytic scission of the benzyl-heteroatom bond with subsequent decarboxylation of the unstable carbamic acid thus formed or treatment with acids. Di-tert-butyloxycarbonyl (Boc) can be removed, for example, by acidic hydrolysis.

Allyloxycarbonyl (Alloc) can be removed, for example, by the action of tetrakis(triphenylphosphine)palladium(0) and a nucleophile.

In a further preferred embodiment, steps (B) and/or (C) take place in the presence of one or more solvents. Step (B) can be performed, for example, in the presence of dichloromethane (DCM), dimethylformamide (DMF) or acetonitrile (MeCN). Step (C) can be performed, for example, in the presence of water/dichloromethane or toluene/tetrabutylammonium iodide (TBAI).

Unicellular or multicellular microorganisms may be triggers for infectious diseases. Administration of at least one pathogen-specific antidote, for example antibiotic, antimycotic or virustat, can reduce the number of pathogens and/or inactivate the pathogen. A pathogen-specific antidote can be administered systemically and/or topically.

In the case of systemic administration, the pathogen-specific antidote is transferred to the blood system and/or lymph system of the body to be treated and is distributed over the entire body in this way. In the case of systemic administration of the pathogen-specific antidote, there may be degradation of the antidote and/or side effects, for example as a result of a biochemical transformation (metabolization) of the antidote.

In the case of topical administration of pathogen-specific antidote, the antidote is applied where it is to act therapeutically, for example on an infected part of the skin, while the healthy skin is not stressed. Thus, systemic side effects can be substantially avoided.

Superficial skin or soft tissue infections need not necessarily be treated by a systemic administration of a pathogen-specific antidote, since the antidote can be applied directly to the infected part of the skin.

The pathogen-specific antidotes known to date, both in the case of systemic and topical administration, have side effects and interactions, some of them severe. Furthermore, in the case of topical administration, unreliable taking of medicaments (compliance) on the part of the patient, especially in the case of use of antibiotics, can result in development of resistance.

An alternative here is the photodynamic inactivation of microorganisms, where resistances to photodynamic inactivation are unknown. Irrespective of the nature of the microorganisms to be controlled and the associated infectious diseases, the number of pathogens is reduced and/or the pathogens are killed. For example, mixtures of various microorganisms, for example fungi and bacteria or different bacterial strains, can be controlled.

In a preferred embodiment, at least one 10H-benzo[g]pteridine-2,4-dione derivative of the formula (1) used in accordance with the invention or a pharmacologically acceptable salt and/or ester and/or complex thereof is used as a photosensitizer in the photodynamic inactivation of microorganisms, preferably in photodynamic therapy.

The 10H-benzo[g]pteridine-2,4-dione derivative of the formula (1) used in accordance with the invention as a photosensitizer in the inactivation of microorganisms, after irradiation with electromagnetic radiation of suitable wavelength and energy density, has a high yield of singlet oxygen.

The electromagnetic radiation is preferably in the visible spectral region, ultraviolet region and/or infrared region. Further preferably, the electromagnetic radiation has a wavelength from a range from 280 to 1000 nm, further preferably from 380 to 1000 nm.

Further preferably, the electromagnetic radiation has an energy density from a range from 1 $\mu W/cm^2$ to 1 $MW/cm^2$, further preferably from 1 $mW/cm^2$ to 1 $kW/cm^2$.

The irradiation time can be varied as a function of the nature of the microorganisms and/or the severity of the infection. The irradiation time is preferably within a range from 1 $\mu$s to 1 h, further preferably from 1 ms to 1000 s.

Preferably, the electromagnetic radiation is generated by a radiation source selected from the group consisting of the sun and artificial radiation sources, for example UV lamp, IR lamp, phosphor lamps, light-emitting diodes, lasers or chemical light.

Furthermore, the inventors have found that, surprisingly, the a 10H-benzo[g]pteridine-2,4-dione derivative of the formula (1) used in accordance with the invention or a pharmacologically acceptable salt and/or ester and/or complex thereof preferably has a high affinity for microorganisms.

On account of the affinity, the 10H-benzo[g]pteridine-2,4-dione derivative of the formula (1) used in accordance with the invention can bind effectively to microorganisms and produce sufficient singlet oxygen locally to inactivate, preferably kill, the microorganisms.

In this preferred use as a photosensitizer, at least one 10H-benzo[g]pteridine-2,4-dione derivative of the formula (1) is bound by microorganisms. After irradiation with electromagnetic radiation of suitable wavelength and energy density, microorganisms are inactivated, preferably killed, by the reactive oxygen species (ROS) formed, preferably oxygen radicals and/or singlet oxygen.

Preferably, the binding of at least one 10H-benzo[g]pteridine-2,4-dione derivative of the formula (1) used in accordance with the invention to microorganisms likewise allows staining or localization of microorganisms. In this way, it is preferably also possible to monitor the progress of the inactivation of microorganisms or of the decolonization.

According to the invention, the term "decolonization" is understood to mean the removal, preferably complete removal, of microorganisms.

In a further preferred embodiment, at least one 10H-benzo[g]pteridine-2,4-dione derivative of the formula (1) used in accordance with the invention or a pharmacologically acceptable salt and/or ester and/or complex thereof is used in the inactivation of unicellular or multicellular microorganisms, selected from the group consisting of viruses, archaea, bacteria, bacterial spores, fungi, for example mycelium fungi and yeasts, fungal spores, protozoa, algae and blood-transmissible parasites.

It is possible with preference to treat surfaces of the body, for example the skin or mucous membrane, of humans and animals, preferably mammals. In this preferred embodiment, at least one 10H-benzo[g]pteridine-2,4-dione derivative of the formula (1) used in accordance with the invention or a pharmacologically acceptable salt and/or ester and/or complex thereof, preferably in a pharmaceutical formulation, is used in the disinfection and/or decolonization of surfaces of skin or soft tissue, preferably with preservation of skin integrity.

In a further preferred embodiment, at least one 10H-benzo[g]pteridine-2,4-dione derivative of the formula (1) used in accordance with the invention or a pharmacologically acceptable salt and/or ester and/or complex thereof is present in a pharmaceutical formulation for topical, preferably nasal, oral, anal, vaginal or dermal, administration.

Topical administration is also understood to mean application on or in the ear, preferably the outer ear. The outer ear comprises the ear cartilage, the pinna, the earlobe and the outer auditory canal or else ear canal, and the outside of the eardrum.

In a further preferred embodiment, at least one 10H-benzo[g]pteridine-2,4-dione derivative of the formula (1) used in accordance with the invention or a pharmacologically acceptable salt and/or ester and/or complex thereof is used for production of a pharmaceutical formulation in the prophylaxis and/or treatment of an infectious, preferably viral, bacterial and/or mycotic, skin disease which is preferably selected from the group consisting of staphylococcal scalded skin syndrome, impetigo, skin abscess, furuncle, carbuncle, phlegmon, cellulitis, acute lymphadenitis, pilonidal cysts, pyoderma, purulent dermatitis, septic dermatitis, suppurative dermatitis, erythrasma, erysipelas, acne vulgaris and fungal infection.

In a further preferred embodiment, at least one 10H-benzo[g]pteridine-2,4-dione derivative of the formula (1) used in accordance with the invention or a pharmacologically acceptable salt and/or ester and/or complex thereof is used for production of a pharmaceutical formulation in wound healing, for example in the event of disrupted healing after surgical interventions.

Preferably, at least one 10H-benzo[g]pteridine-2,4-dione derivative of the formula (1) used in accordance with the invention or a pharmacologically acceptable salt and/or ester and/or complex thereof, or a pharmaceutical formulation comprising at least one inventive 10H-benzo[g]pteridine-2,4-dione derivative of the formula (1) or a pharmacologically acceptable salt and/or ester and/or complex thereof is used in the disinfection and/or reduction of the microbe count in infected wounds.

In a further preferred embodiment, at least one 10H-benzo[g]pteridine-2,4-dione derivative of the formula (1) used in accordance with the invention or a pharmacologically acceptable salt and/or ester and/or complex thereof is used for production of a pharmaceutical formulation in the prophylaxis and/or treatment of infectious, preferably viral, bacterial and/or mycotic, disorders of the ear, of the upper respiratory pathway, of the oral cavity, of the throat, of the larynx, of the lower respiratory pathway and/or of the esophagus.

The prevalence of pathogenic microorganisms is, for example, the main cause of infections in the oral cavity. The problem occurs that the microorganisms are organised synergetically in biofilms of extremely complex structure. These biofilms, for example plaque or dental deposits, consist of several layers of complex structure and contain proteins, carbohydrates, phosphates and microorganisms. Dental deposits arise particularly where tooth surfaces cannot be kept free of deposits by natural or artificial cleaning. This fact makes it difficult to find access to the microorganisms incorporated within the biofilm.

Conventional treatments, for example antibiotics and rinse solutions or mechanical tooth cleaning, can be used only to a limited degree, since they do not directly affect the bacteria, for example in the case of tooth cleaving, can be dosed and applied only with difficulty, for example in the case of antibiotics and rinse solutions, or general application is unjustified because of adverse accompanying phenomena.

In a preferred embodiment, at least one 10H-benzo[g]pteridine-2,4-dione derivative of the formula (1) used in accordance with the invention or a pharmacologically compatible salt and/or ester and/or complex thereof is used as a photosensitizer in the photodynamic inactivation of microorganisms in the oral cavity.

In a further preferred embodiment, at least one 10H-benzo[g]pteridine-2,4-dione derivative of the formula (1) used in accordance with the invention or a pharmacologically acceptable salt and/or ester and/or complex thereof i used for production of a pharmaceutical formulation in the treatment and/or prophylaxis of an infectious, preferably viral, bacterial and/or mycotic, disorder of the dental tissue, preferably plaque, caries or pulpitis, and/or infectious, preferably viral, bacterial and/or mycotic, disorder of the periodontium, preferably gingivitis, paradontitis, endodontitis or periimplantitis.

In a further preferred embodiment, at least one 10H-benzo[g]pteridine-2,4-dione derivative of the formula (1) used in accordance with the invention or a pharmacologically acceptable salt and/or ester and/or complex thereof, or a pharmaceutical formulation comprising at least one inventive 10H-benzo[g]pteridine-2,4-dione derivative of the formula (1) or a pharmacologically acceptable salt and/or ester and/or complex thereof, is used in the cleaning of teeth, dentures and/or dental braces.

In a further preferred embodiment, at least one 10H-benzo[g]pteridine-2,4-dione derivative of the formula (1) used in accordance with the invention or a pharmacologically acceptable salt and/or ester and/or complex thereof, or a pharmaceutical formulation comprising at least one inventive 10H-benzo[g]pteridine-2,4-dione derivative of the formula (1) or a pharmacologically acceptable salt and/or ester and/or complex thereof, is used in the nasal decolonization of microorganisms.

For example, methicillin-resistant *Staphylococcus aureus* (MRSA) strains persist for months in the event of nasal colonization, and have a high environmental resistance. Therefore, nasal decolonization, i.e. removal of the microorganisms, generally also reduces colonization in other parts of the body.

The present invention further relates to the use of a pharmaceutical composition comprising at least one 10H-benzo[g]pteridine-2,4-dione derivative of the formula (1) or a pharmacologically acceptable salt and/or ester and/or complex thereof as a photosensitizer in the inactivation of microorganisms.

The pharmaceutical composition is preferably produced by mixing at least one compound of the formula (1) or a pharmacologically acceptable salt and/or ester and/or complex thereof with one or more physiologically acceptable excipient(s) and converted to a suitable administration form.

A suitable administration form of the inventive pharmaceutical composition is preferably selected from the group consisting of ointment, cream, gel, lotion, shake lotion, solution, for example in droplet or spray form, powder, microcapsule and paste.

The inventive pharmaceutical formulation can be applied topically, preferably nasally, orally, anally, vaginally or dermally.

Useful physiologically acceptable excipients include the pharmaceutically customary liquid or solid fillers and extenders, solvents, emulsifiers, glidants, flavor correctors, dyes and/or buffer substances.

In a further preferred embodiment, the pharmaceutical composition comprises an effective amount of at least one 10H-benzo[g]pteridine-2,4-dione derivative of the formula (1) used in accordance with the invention or of a pharmacologically acceptable salt and/or ester and/or complex thereof, the effective amount being from 0.01 µg to 1000 µg per gram of the composition, preferably from 0.1 µg to 500 µg per gram of the composition.

In a preferred embodiment of the invention, the pharmaceutical composition comprises at least one 10H-benzo[g]pteridine-2,4-dione derivative of the formula (1) used in accordance with the invention or a pharmacologically acceptable salt and/or ester and/or complex thereof and at least one further pharmaceutically active constituent.

Preferably, the at least one further pharmaceutically active constituent is selected from the group consisting of antibiotics, antimycotics, virustatics, antihistamines, sympathomimetics, antihemorrhagics, emollients and skin protection agents, analgesics, disinfectants, immunosera and immunoglobulins, antiparasitic substances, insecticides, repellents and corticosteroids.

In a further preferred embodiment, at least one 10H-benzo[g]pteridine-2,4-dione derivative of the formula (1) used in accordance with the invention or a pharmacologically acceptable salt and/or ester and/or complex thereof, or a pharmaceutical formulation comprising at least one inventive 10H-benzo[g]pteridine-2,4-dione derivative of the formula (1) or a pharmacologically acceptable salt and/or ester and/or complex thereof, is applied by the user him/herself and, optionally, irradiated subsequently with a suitable radiation source which generates electromagnetic radiation of suitable wavelength and energy density.

In a further preferred embodiment, at least one 10H-benzo[g]pteridine-2,4-dione derivative of the formula (1) used in accordance with the invention or a pharmacologically acceptable salt and/or ester and/or complex thereof, or a formulation comprising at least one 10H-benzo[g]pteridine-2,4-dione derivative of the formula (1) used in accordance with the invention or a pharmacologically acceptable salt and/or ester and/or complex thereof, is used in the inactivation of microorganisms in medical blood products.

In a preferred embodiment, at least one 10H-benzo[g]pteridine-2,4-dione derivative of the formula (1) used in accordance with the invention or a pharmacologically acceptable salt and/or ester and/or complex thereof is used for inactivation of microorganisms on surfaces of all kinds. Further preferably, the 10H-benzo[g]pteridine-2,4-dione derivative used in accordance with the invention is used in surface cleaning and/or coating, preferably of medical products, food and drink packaging or hygiene articles.

Further preferably, at least one 10H-benzo[g]pteridine-2,4-dione derivative of the formula (1) used in accordance with the invention or a pharmacologically acceptable salt and/or ester and/or complex thereof is applied to and/or introduced onto surfaces and, optionally, subsequently irradiated with a suitable radiation source which generates electromagnetic irradiation of suitable wavelength and energy density. Preferably, the at least one 10H-benzo[g]pteridine-2,4-dione derivative of the formula (1) used in accordance with the invention or a pharmacologically acceptable salt and/or ester and/or complex thereof brings about "self-disinfection" of the surface during the irradiation.

The irradiation may directly follow the treatment of the surface with at least one 10H-benzo[g]pteridine-2,4-dione derivative of the formula (1) used in accordance with the invention or a pharmacologically acceptable salt and/or ester and/or complex thereof, preferably the application of the at least one inventive 10H-benzo[g]pteridine-2,4-dione derivative of the formula (1) or a pharmacologically acceptable salt and/or ester and/or complex thereof to the surface and/or introduction of the at least one inventive 10H-benzo[g]pteridine-2,4-dione derivative of the formula (1) or a pharmacologically acceptable salt and/or ester and/or complex thereof into the surface, and/or be effected at a later juncture.

Further preferably, articles having thermally limited shelf life are treated, for example articles made from thermoplastics, or articles which are attacked by disinfectants.

Articles having a thermally limited shelf life can, for example, be only inadequately sterilized, since they lose shape or become brittle at relatively high temperatures.

Furthermore, in the event of improper and/or excessive use of disinfectants, development of resistance can result from selection of robust microorganisms when, for example, the active ingredient concentration and contact time and hence the microbe-reducing effect is too low.

In a further-preferred embodiment, at least one 10H-benzo[g]pteridine-2,4-dione derivative of the formula (1) used in accordance with the invention or a pharmacologically acceptable salt and/or ester and/or complex thereof is used for inactivation of microorganisms on surfaces of medical products, preferably invasive medical implements, for example catheters, hollow probes, tubes or needles.

The medical products are preferably selected from wound dressings, bandages, catheters; hollow probes, tubes and needles.

Further preferably, medical products are also understood to mean dental impressions or dentures, for example prostheses, crowns or implants.

Preferably, a treatment of the surface of medical products with at least one 10H-benzo[g]pteridine-2,4-dione derivative of the formula (1) used in accordance with the invention or a pharmacologically acceptable salt and/or ester and/or complex thereof, and/or coating and/or immobilization of at least one 10H-benzo[g]pteridine-2,4-dione derivative used in accordance with the invention on the surface of medical products and subsequent irradiation with electromagnetic radiation of suitable wavelength and energy density, reduces, preferably prevents, the colonization of microorganisms on the surfaces treated.

The irradiation may directly follow the treatment of the surface with at least one 10H-benzo[g]pteridine-2,4-dione derivative of the formula (1) used in accordance with the invention or a pharmacologically acceptable salt and/or ester and/or complex thereof, preferably the application of the at least one inventive 10H-benzo[g]pteridine-2,4-dione derivative of the formula (1) or a pharmacologically acceptable salt and/or ester and/or complex thereof to the surface and/or introduction of the at least one 10H-benzo[g]pteridine-2,4-dione derivative of the formula (1) used in accordance with the invention or a pharmacologically acceptable salt and/or ester and/or complex thereof into the surface, and/or be effected at a later juncture, before or during the use of the treated medical product.

In a further-preferred use of the at least one 10H-benzo[g]pteridine-2,4-dione derivative of the formula (1) used in accordance with the invention or a pharmacologically acceptable salt and/or ester and/or complex, or of a pharmacologically acceptable salt and/or ester and/or complex thereof, in wound dressings and/or bandages, for example cotton gauze, irradiation with electromagnetic radiation of suitable wavelength and energy density can be effected during or after the application of a dressing and/or bandage comprising the at least one 10H-benzo[g]pteridine-2,4-dione derivative used in accordance with the invention or a pharmacologically acceptable salt and/or ester and/or complex thereof, as a result of which there is a subsequent reduction, preferably inactivation, of microorganisms in the wound region or treated parts of the skin.

In a further preferred embodiment, the wound dressing and/or bandage comprises, as well as at least one 10H-benzo[g]pteridine-2,4-dione derivative of the formula (1) used in accordance with the invention or a pharmacologically acceptable salt and/or ester and/or complex thereof, or of a pharmacologically acceptable salt and/or ester and/or complex thereof, further constituents, preferably absorbents, for example calcium alginate or polyurethane foam, or further pharmaceutically active substances.

In a further preferred embodiment, at least one 10H-benzo[g]pteridine-2,4-dione derivative of the formula (1) used in accordance with the invention or a pharmacologically acceptable salt and/or ester and/or complex thereof is used for inactivation of microorganisms on surfaces of food and drink packaging.

In a further preferred embodiment, at least one 10H-benzo[g]pteridine-2,4-dione derivative used in accordance with the invention is used for inactivation of microorganisms in a liquid or a liquid, preferably aqueous, formulation, for example emulsion paint.

The liquid is preferably water.

In this case, at least one 10H-benzo[g]pteridine-2,4-dione derivative used in accordance with the invention can be used for treatment of water for the drinks and food industry, the pharmaceutical, chemical and cosmetics industry, the electrical industry. In addition, at least one inventive 10H-benzo[g]pteridine-2,4-dione derivative of the formula (1) or a pharmacologically acceptable salt and/or ester and/or complex thereof can be used in drinking water and rainwater treatment, the treatment of wastewater, or in the treatment of water for use in air conditioning.

In this preferred use of at least one 10H-benzo[g]pteridine-2,4-dione derivative of the formula (1) used in accordance with the invention or a pharmacologically acceptable salt and/or ester and/or complex thereof, the liquid or the liquid formulation can subsequently be irradiated with a suitable radiation source which generates electromagnetic radiation of suitable wavelength and energy density. Preferably, the 10H-benzo[g]pteridine-2,4-dione derivative of the formula (1) used in accordance with the invention or a pharmacologically acceptable salt and/or ester and/or complex thereof brings about "self-disinfection" of the liquid or of the liquid formulation during the irradiation.

In a further preferred use of the at least one 10H-benzo[g]pteridine-2,4-dione derivative of the formula (1) used in accordance with the invention or a pharmacologically acceptable salt and/or ester and/or complex thereof, the 10H-benzo[g]pteridine-2,4-dione derivative may be bound to a solid carrier and thus be used as part of a solid matrix. More preferably, at least one 10H-benzo[g]pteridine-2,4-dione derivative of the formula (1) used in accordance with the invention or a pharmacologically acceptable salt and/or ester and/or complex thereof bound to a solid carrier is introduced into the liquid to be treated, preferably water or blood.

A particularly preferred carrier is a polymer which carries at least one 10H-benzo[g]pteridine-2,4-dione derivative of the formula (1) used in accordance with the invention or a pharmacologically acceptable salt and/or ester and/or complex thereof in a covalently bonded manner. This composition, comprising the carrier and at least one 10H-benzo[g]pteridine-2,4-dione derivative of the formula (1) used in accordance with the invention or a pharmacologically acceptable salt and/or ester and/or complex thereof, develops antimicrobial activity as soon as it is exposed to electromagnetic radiation of suitable wavelength and energy density.

The present invention further relates to a coated article which comprises and/or has been coated with at least one 10H-benzo[g]pteridine-2,4-dione derivative used in accordance with the invention.

The surface of the coated article preferably comprises at least one inventive 10H-benzo[g]pteridine-2,4-dione derivative of the formula (1) or a pharmacologically acceptable salt and/or ester and/or complex thereof.

The coated article can subsequently be irradiated with a suitable radiation source which generates the electromagnetic radiation of suitable wavelength and energy density. Preferably, the 10H-benzo[g]pteridine-2,4-dione derivative of the formula (1) used in accordance with the invention or a pharmacologically acceptable salt and/or ester and/or complex thereof brings about "self-disinfection" of the surface of the coated article during the irradiation.

The irradiation may directly follow the treatment of the coated article with at least one 10H-benzo[g]pteridine-2,4-dione derivative of the formula (1) used in accordance with the invention or a pharmacologically acceptable salt and/or ester and/or complex thereof, preferably the application of the at least one 10H-benzo[g]pteridine-2,4-dione derivative of the formula (1) used in accordance with the invention or a pharmacologically acceptable salt and/or ester and/or complex thereof to the surface of the coated article and/or introduction of the at least one 10H-benzo[g]pteridine-2,4-dione derivative of the formula (1) used in accordance with the invention or a pharmacologically acceptable salt and/or ester and/or complex thereof into the surface of the coated article, and/or be effected at a later juncture, preferably before or during the use of the coated article.

Suitable articles are preferably selected from the group consisting of medical products, food and drink packaging, and hygiene articles.

In a further preferred embodiment of the coated article, particles coated with at least one 10H-benzo[g]pteridine-2,4-dione derivative of the formula (1) used in accordance with the invention or a pharmacologically acceptable salt and/or ester and/or complex thereof are, for example, inorganic or organic particles.

Further preferably, the particles comprise at least one 10H-benzo[g]pteridine-2,4-dione derivative of the formula (1) used in accordance with the invention or a pharmacologically acceptable salt and/or ester and/or complex thereof, which is covalently bonded to the particles.

The invention is illustrated hereinafter by figures and examples, without being restricted thereto.

Synthesis of the Compounds Used:

All substances were prepared analogously to literature methods:

1,2-dinitro-4,5-dimethylbenzene (31) according to: A. Monge, J. A. Palop, A. López de Ceráin, V. Senador, F. J. Martinez-Crespo, Y. Sainz, S. Narro, E. Garcia, C. de Miguel, M. González, E. Hamilton, A. J. Barker, E. D. Clarke, D. T. Greenhow, J. Med. Chem. 1995, 38, 1786-1792; T. Sugaya, K. Nobuyuki, A. Sakaguchi, S. Tomioka, Synthesis 1995, 1257-1262; R. R. Holmes, R. P. Bayer, J. Am. Chem. Soc. 1960, 82, 3454-3456, N-[2-({[(tert-butyl)oxy]carbonyl}amino)ethyl]-4,5-dimethyl-2-nitroaniline (32) according to J. Butenandt, R. Epple, E.-U. Wallenborn, A. P. M. Eker, V. Gramlich, T. Carell, Chem. Eur. J. 2000, 6, No. 1, 62-72, N-(3'-oxabut-1'-yl)-4,5-dimethyl-2-nitroaniline (33) and 10-(2'-methoxyethyl)-7,8-dimethyl-10H-benzo[g]pteridine-2,4-dione (37) according to R. Epple, E.-U. Wallenborn, T. Carell, J. Am. Chem. Soc. 1997, 119, 7440-7451, 10-aminoethyl-7,8-dimethyl-10H-benzo[g]pteridine-2,4-dione hydrochloride (39) according to J. Butenandt, R. Epple, E.-U. Wallenborn, A. P. M. Eker, V. Gramlich, T. Carell, Chem. Eur. J. 2000, 6, No. 1, 62-72, and 10-(8'-amino-3',6'-dioxaoct-1'-yl)-7,8-dimethylbenzo[g]pteridine-2,4-dione hydrochloride (40) and 3-(2'-aminoeth-1'-yl)-7,8-dimethyl-10-(3"-oxabut-1"-yl)benzo-[g]pteridine-2,4-dione (42) according to J. Svoboda, H. Schmaderer, B. König, Chem. Eur. J. 2008, 14, 1854-1865.

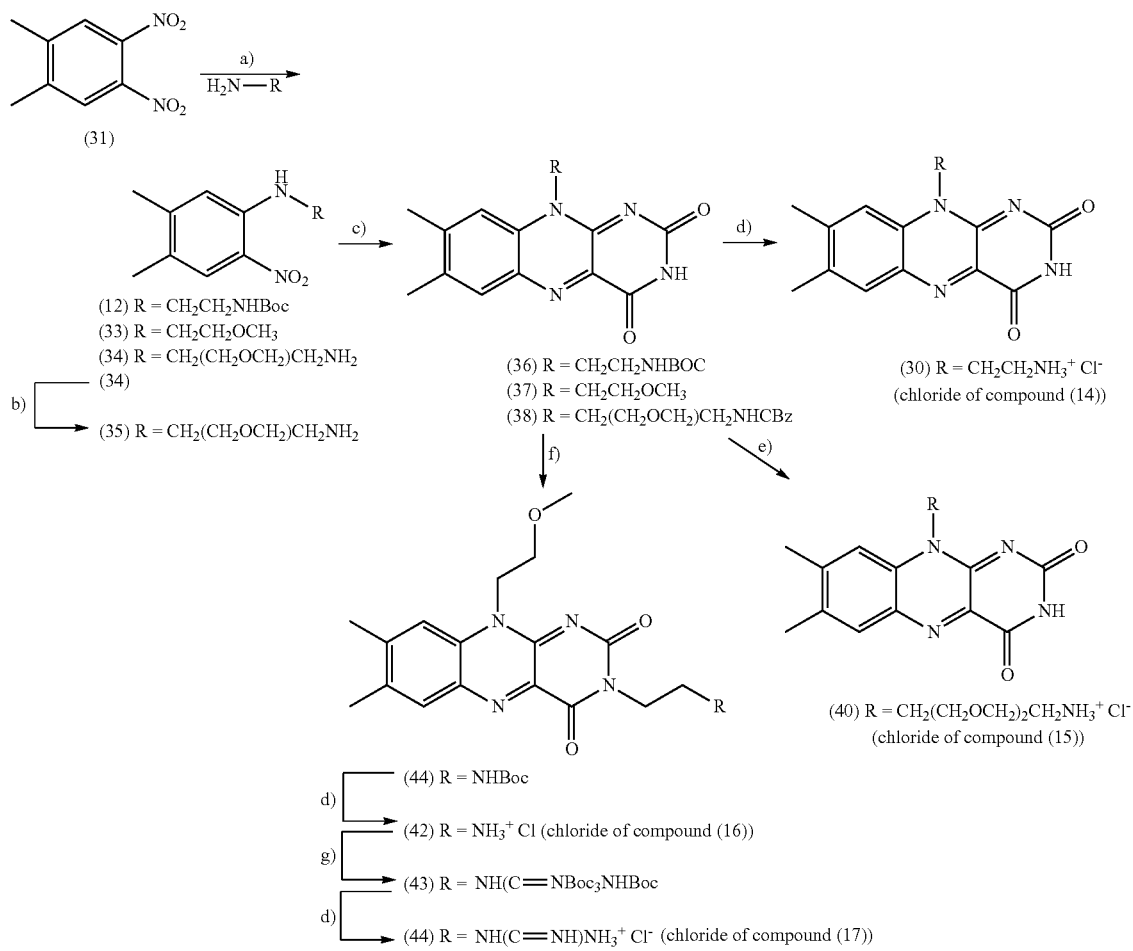

In the synthesis of compounds (39), (40), (42) and (44), the following reaction conditions were selected:

a) EtOH, NEt₃, reflux, 2d; b) Cbz-Cl, DCM, NEt₃, 30 min., 0° C.; c) Pd/C, H₂, HOAc, 14h, then alloxane monohydrate, H₃B0₃, HOAc, RT, 2d; d) HCl, Et₂O, DCM, RT, 10h; e) ZnBr₂, HOAc, RT, overnight; HCl, freeze-drying; f) 2-N-Boc-aminoethyl bromide, Cs₂CO₃, DMF, RT, 2d; g) 1,3-N,N''-di-Boc-2-methylisothiourea, DCC, NEt₃, DMF, 2d, RT;

Phototoxicity Experiments a) Production of the Test Plates and Bacterial Strains A sample of the bacterial strain *Staphylococcus aureus* (ATCC number: 25923) or *Escherichia coli* (ATCC number: 25922) was taken from a cryogenically frozen culture, isolated on Müller-Hinton agar plates and cultivated under aerobic conditions at 37° C. in an overnight culture. Thereafter, 5 ml of Müller-Hinton liquid medium were inoculated with a smear of the bacterial culture (single colony) and incubated at 37° C. overnight. The bacterial suspension thus obtained was centrifuged at 2500 rpm for 10 min and the bacterial pellet obtained was resuspended in 5 ml of sterile PBS. The optical density of the bacterial suspensions for the phototoxicity tests was $OD_{600nm}=0.6$, which corresponds to a bacteria count of $\sim 1-8 \times 10^{8-12}$ bacteria per ml. The biochemical analysis and resistance determination of the bacteria were conducted with the VITEK2 system according to the M100-S14 guidelines from the NCCLS (2004).

To check sensitivity of medically significant pathogens against antibiotics and sulfonamides, in accordance with the NCCLS guidelines, Müller-Hinton media were used (Deutsche Gesellschaft für Hygiene und Mikrobiologie (DGHM), Institute of Hygiene and Microbiology, University of Bonn, Germany):

a) Müller-Hinton broth (Oxoid, Wesel, Germany)
2.0 g/l beef, dried infusion from 300 g, 17.5 g/l casein hydrolyzate,
1.5 g/l starch, pH: 7.4+0.2 b) Müller-Hinton agar (Oxoid, Wesel, Germany)
2.0 g/l beef, dried infusion from 300 g, 17.5 g/l casein hydrolyzate,
1.5 g/l starch, pH: 7.4+0.2
13 g/l agar-agar b) Procedure for the Phototoxicity Test:

200 μl of a bacterial suspension (bacterial density: $10^8$-$10^{12}$/ml) were incubated with 200 μl of each of various concentrations of the photosensitizers to be tested at room temperature for 10 min or 30 min. Thereafter, the bacteria were washed twice with distilled water and resuspended in 200 μl of distilled water, and the entire volume was transferred to a 96-well microtiter plate and then irradiated. The photosensitizers used were dissolved in distilled water and various dilution series were prepared (0 μM, 1 μM, 10 μM, 100 μM).

For sensitization, the Omnicure Series 2000 lamp (Photonics Solutions Inc., Edinburgh, UK) was used, which emits light from a range from 390 nm to 500 nm and has emission maxima $E_{max}$ at 405 nm and 436 nm. The power applied in each case was 50 mW/cm$^2$.

Irradiated and unirradiated samples were used as controls. Likewise run were bacterial suspensions incubated only with photosensitizer (dark control).

The determination of the colony-forming units (CFU) per ml was conducted by the method published by Miles and Misra (Miles, A A; Misra, S S, Irwin, J O (1938 November). "The estimation of the bactericidal power of the blood.". *The Journal of hygiene* 38 (6): 732-49). For this purpose, serial dilutions from 10$^{-2}$ to 10$^{-9}$ of the corresponding bacterial suspension were prepared. 3×20 μl of each of the corresponding bacterial dilutions were then dripped onto Müller-Hinton plates and incubated at 37° C. for 24 h. Thereafter, the number of surviving colony-forming units (CFU) was determined. Each of the experiments was repeated three times.

C) Result of the Phototoxicity Experiments:

The results of the phototoxicity experiments are shown in FIGS. 1-4.

FIGS. 1-4 show the logarithmic decreases in the CFU/ml 24 h after irradiation and the corresponding controls (only irradiated bacteria; bacteria incubated with photosensitizer but not irradiated; untreated bacteria) for the respective photosensitizer specified.

Each of the colony-forming units (CFU) per ml reported is the median from three experiments.

FIG. 1 shows the effect of flavin FL-01 (chloride of the compound having the formula (14)) on *E. coli* and *S. aureus*.

Figure 1A:
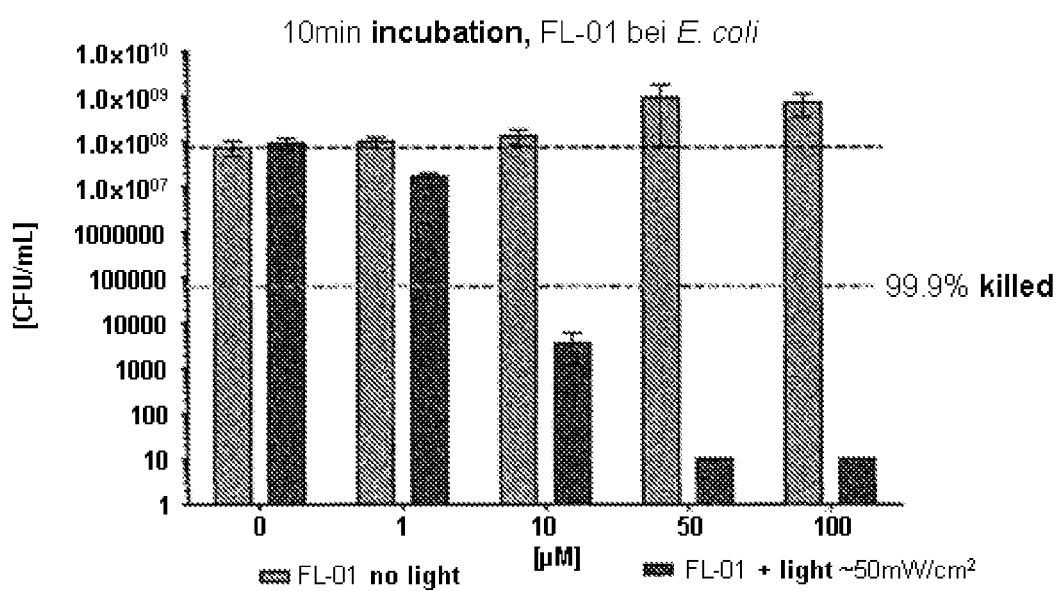

FIG. 1a: *E. coli* samples were incubated with various concentrations (0 μM, 1 μM, 10 μM, 50 μM, 100 μM) of flavin FL-01 for 10 min. Subsequently, the samples were either irradiated at 50 mW/cm$^2$ (210 sec; 10.5 J/cm$^2$) (dark gray bar) or not irradiated (light gray bar). After 24 h, the surviving colonies were counted (CFU/ml). The black line indicates the dark control reference (0 μM flavin FL-01, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 1B:
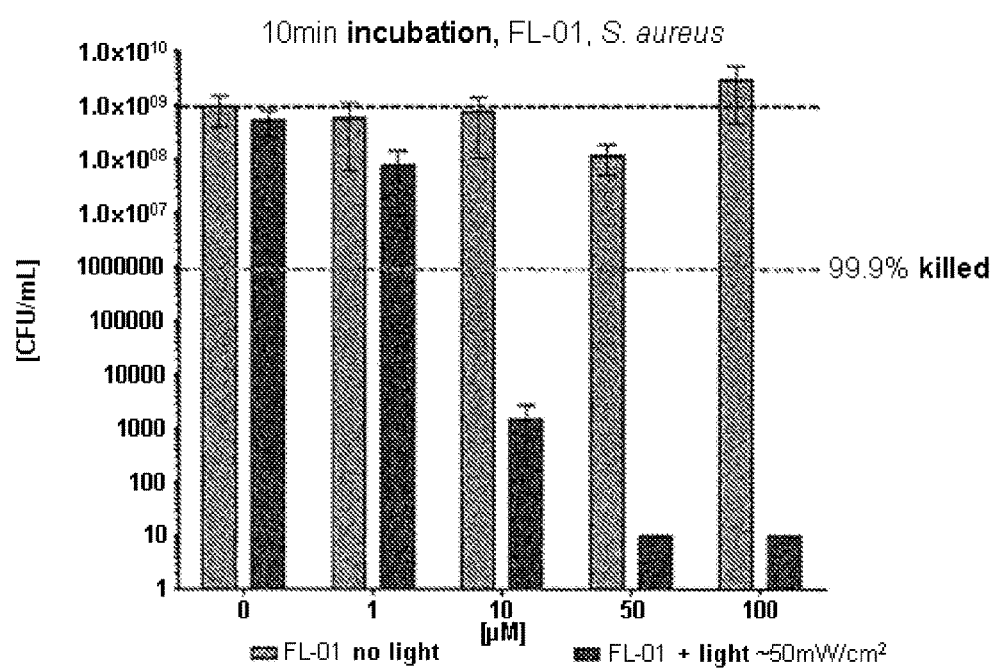

FIG. 1b: *S. aureus* samples were incubated with various concentrations (0 μM, 1 μM, 10 μM, 50 μM, 100 μM) of flavin FL-01 for 10 min. Subsequently, the samples were either irradiated at 50 mW/cm$^2$ (210 sec; 10.5 J/cm$^2$) (dark gray bar) or not irradiated (light gray bar). After 24 h, the surviving colonies were counted (CFU/ml). The black line indicates the dark control reference (0 μM flavin FL-01, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 2:
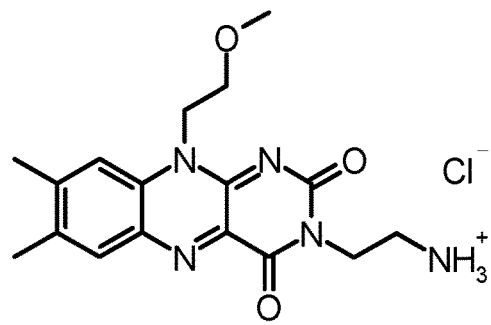

FIG. 2 shows the effect of flavin FL-03 (chloride of the compound having the formula (16)) on *E. coli* and *S. aureus*.

Figure 2A:
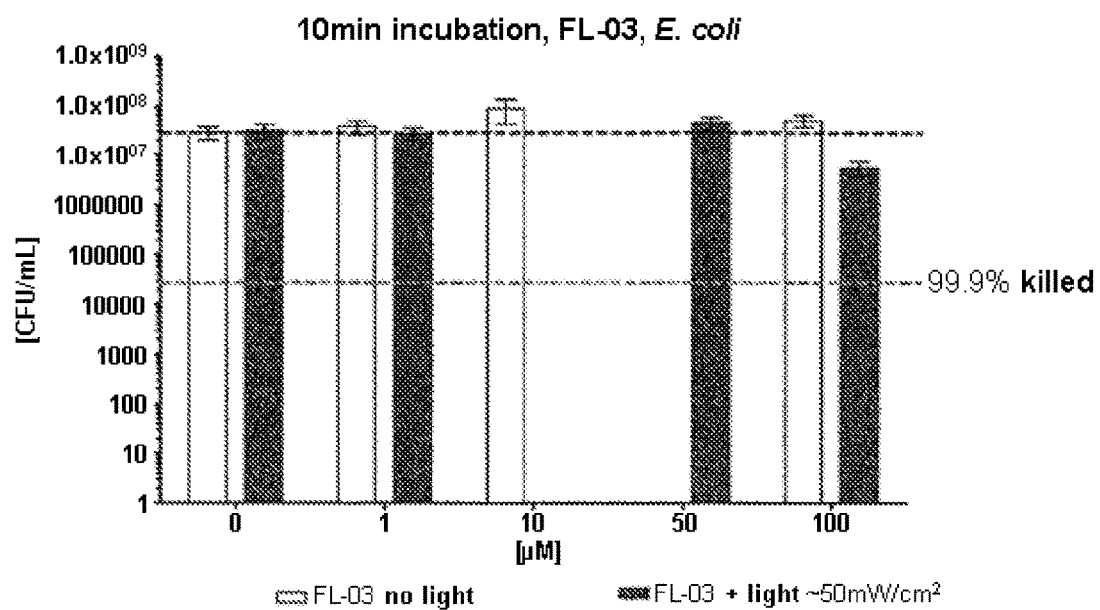

FIG. 2a: *E. coli* samples were incubated with various concentrations (0 μM, 1 μM, 10 μM, 50 μM, 100 μM) of flavin FL-03 for 10 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 μM flavin FL-03, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 2B:
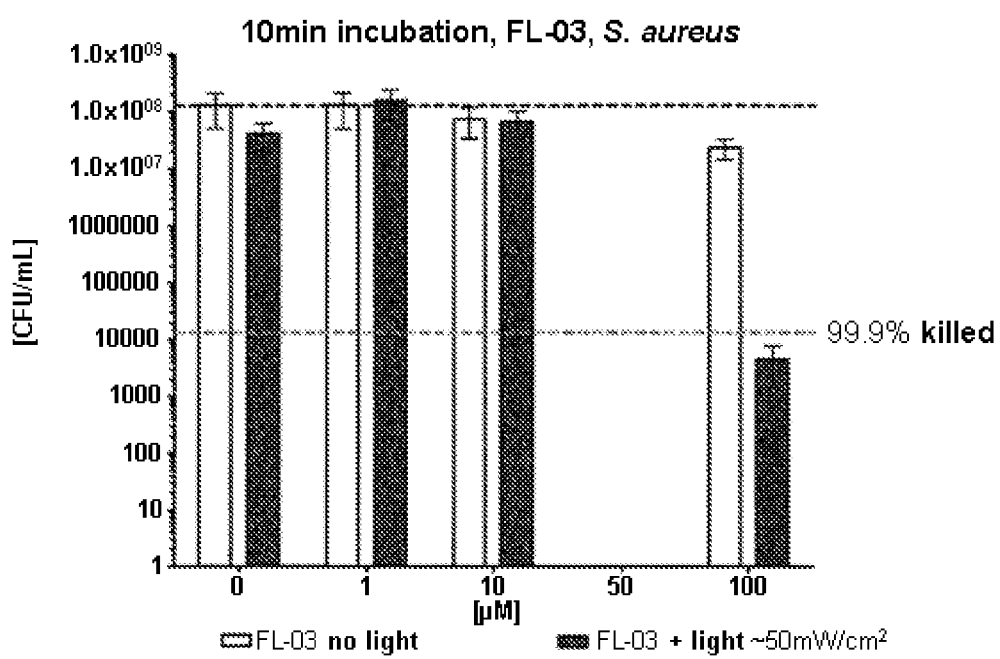

FIG. 2b: *S. aureus* samples were incubated with various concentrations (0 μM, 1 μM, 10 μM, 100 μM) of flavin FL-03 for 10 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 μM flavin FL-03, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 2C:
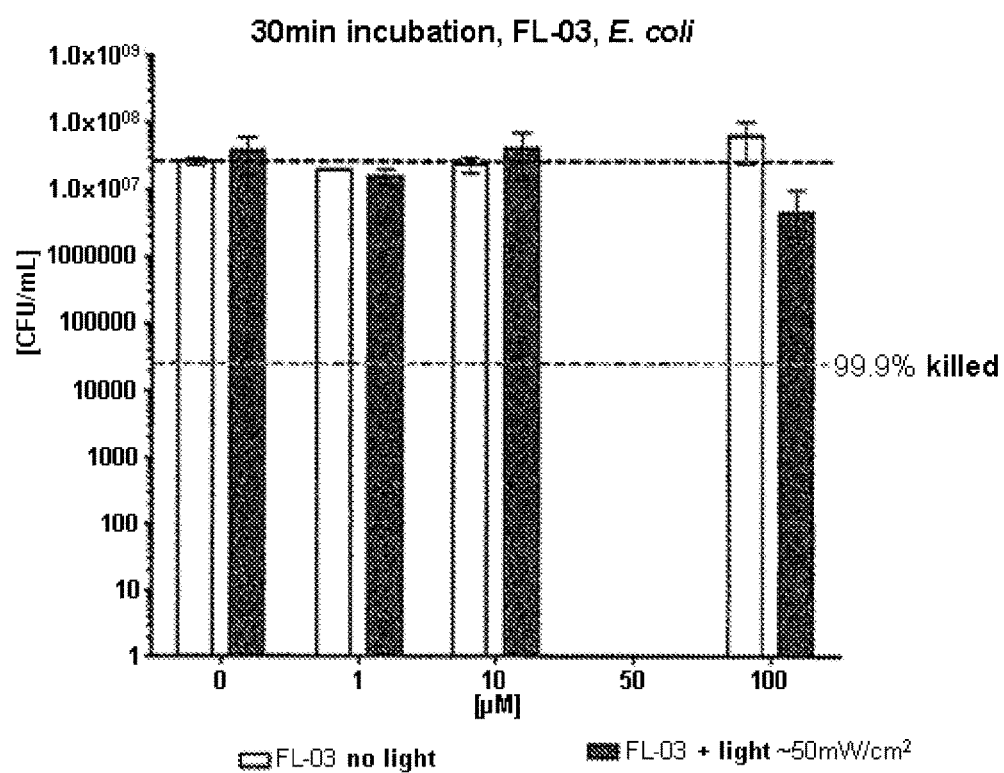

FIG. 2c: *E. coli* samples were incubated with various concentrations (0 μM, 1 μM, 10 μM, 100 μM) of flavin FL-03 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 μM flavin FL-03, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 2D:
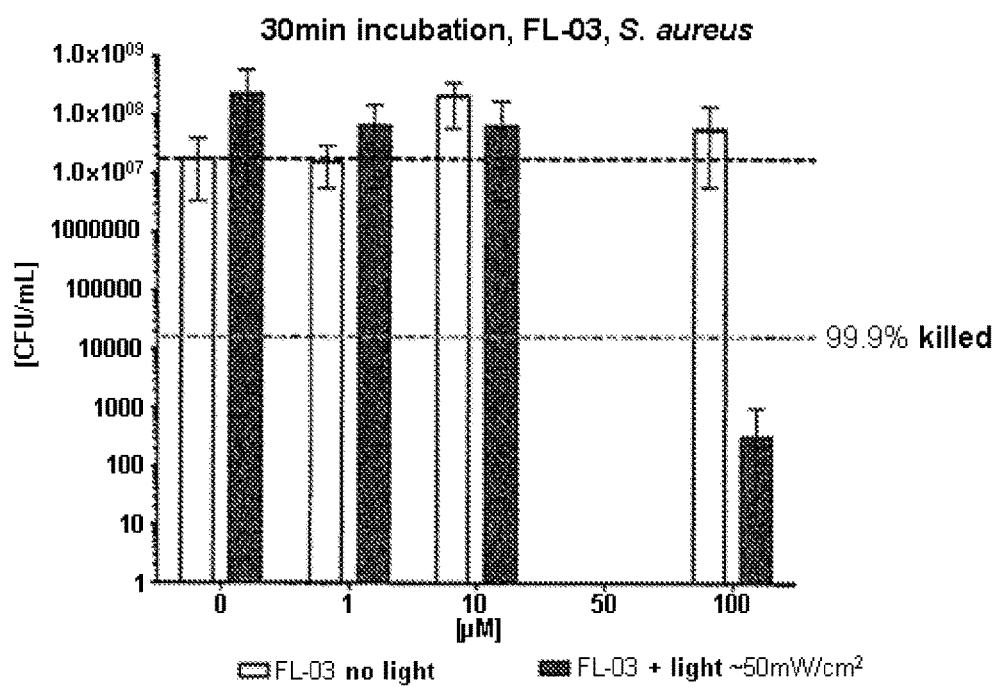

FIG. 2d: *S. aureus* samples were incubated with various concentrations (0 μM, 1 μM, 10 μM, 100 μM) of flavin FL-03 for 30 min. Subsequently, the samples were either irradiated at 50 mW/cm$^2$ (210 sec; 10.5 J/cm$^2$) (dark gray bar) or not irradiated (white bar). After 24 h, the surviving colonies were counted (CFU/ml). The black line indicates the dark control reference (0 μM flavin FL-03, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 3:
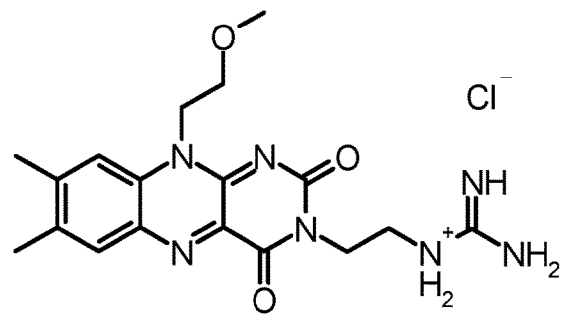

FIG. 3 shows the effect of flavin FL-04 (chloride of the compound having the formula (17)) on *E. coli* and *S. aureus*.

Figure 3A:
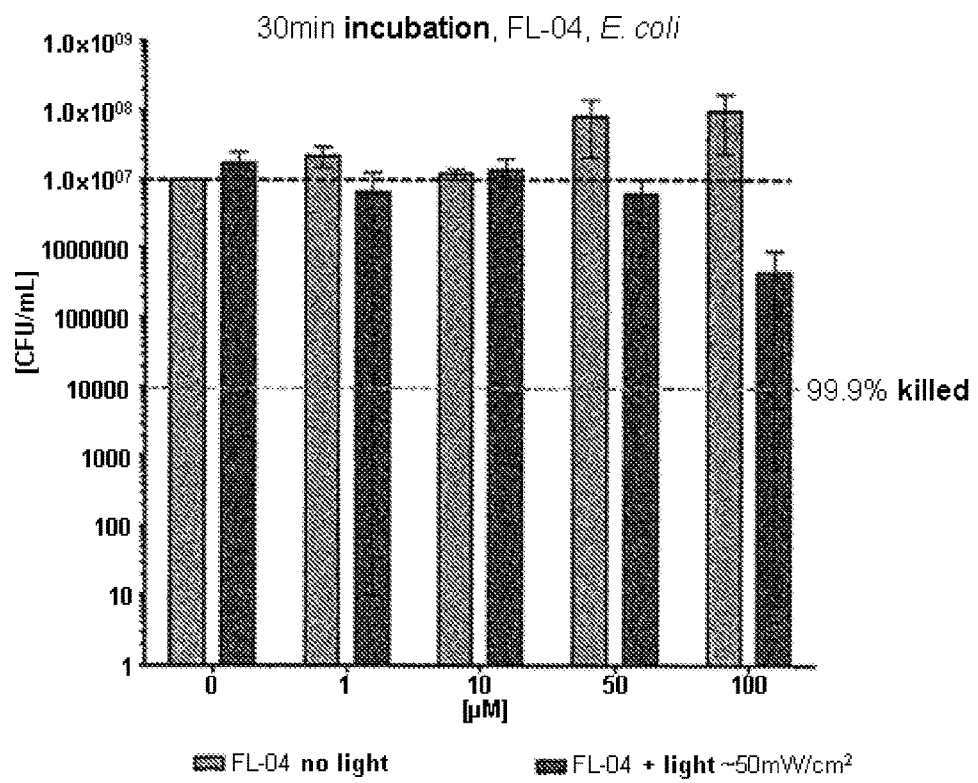

FIG. 3a: *E. coli* samples were incubated with various concentrations (0 μM, 1 μM, 10 μM, 50 μM, 100 μM) of flavin FL-04 for 30 min. Subsequently, the samples were either irradiated at 50 mW/cm$^2$ (210 sec; 10.5 J/cm$^2$) (dark gray bar) or not irradiated (light gray bar). After 24 h, the surviving colonies were counted (CFU/ml). The black line indicates the dark control reference (0 μM flavin FL-04, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 3B:
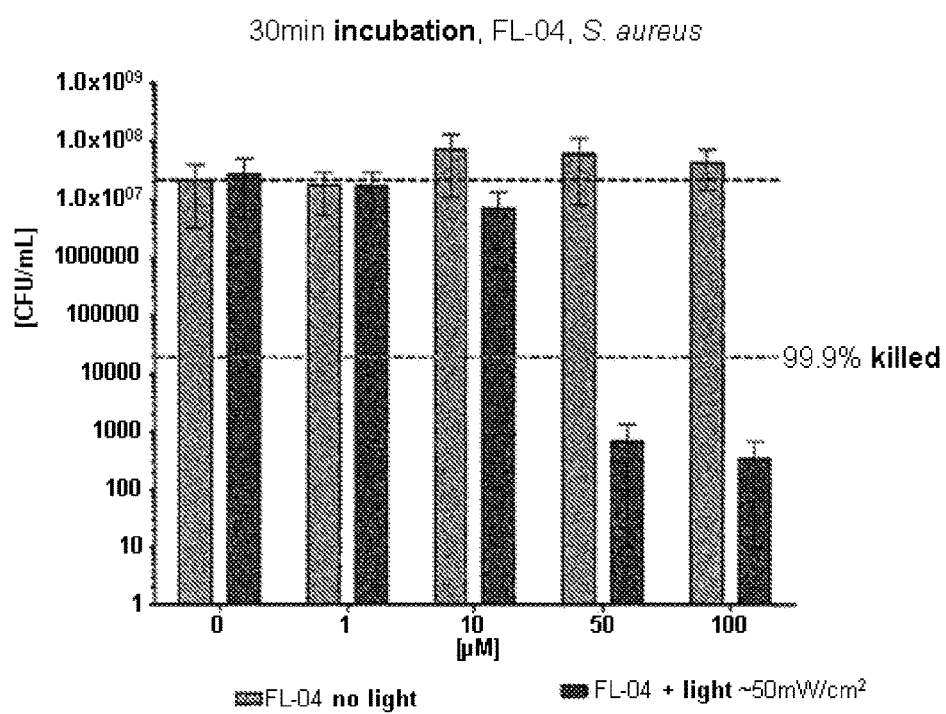

FIG. 3b: *S. aureus* samples were incubated with various concentrations (0 μM, 1 μM, 10 μM, 50 μM, 100 μM) of flavin FL-04 for 30 min. Subsequently, the samples were either irradiated at 50 mW/cm$^2$ (210 sec; 10.5 J/cm$^2$) (dark gray bar) or not irradiated (light gray bar). After 24 h, the surviving colonies were counted (CFU/ml). The black line indicates the dark control reference (0 μM flavin FL-04, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 4:
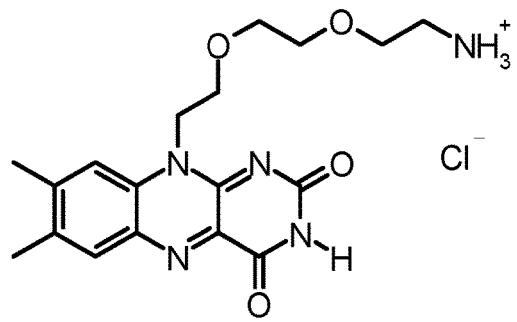

FIG. 4 shows the effect of flavin FL-05 (chloride of the compound having the formula (15)) on *E. coli* and *S. aureus*.

Figure 4A:
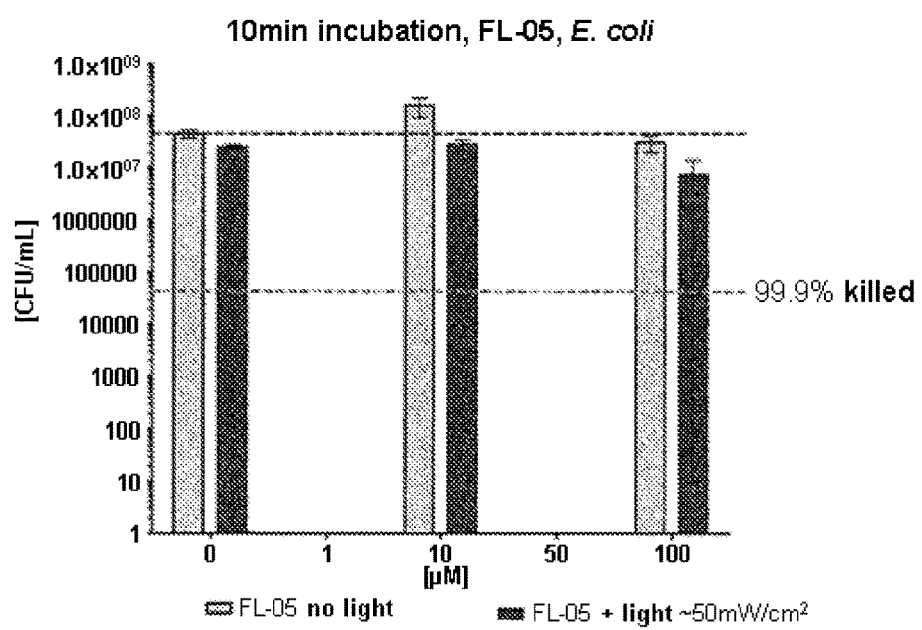

FIG. 4a: *E. coli* samples were incubated with various concentrations (0 μM, 10 μM, 100 μM) of flavin FL-05 for 10 min. Subsequently, the samples were either irradiated at 50 mW/cm$^2$ (210 sec; 10.5 J/cm$^2$) (dark gray bar) or not irradiated (light gray bar). After 24 h, the surviving colonies were counted (CFU/ml). The black line indicates the dark control reference (0 μM flavin FL-05, no light). The dotted line marked "99.9% killed" indicates a decrease in the CFU/ml by 3 log$_{10}$ stages; this corresponds to a decrease by 99.9% ("antibacterial action"). N=3; median CFU/ml±SEM.

Figure 4B:
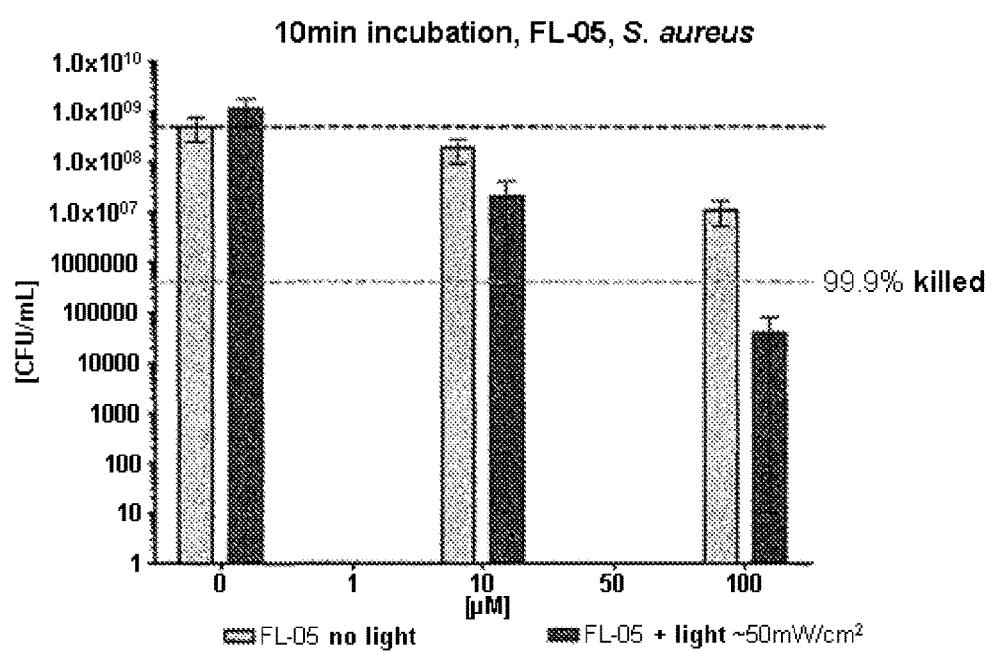

FIG. 4b: *S. aureus* samples were incubated with various concentrations (0 μM, 10 μM, 100 μM) of flavin FL-05 for 10 min. Subsequently, the samples were either irradiated at 50 mW/cm² (210 sec; 10.5 J/cm²) (dark gray bar) or not irradiated (light gray bar). After 24 h, the surviving colonies were counted (CFU/ml). The black line indicates the dark control reference (0 μM flavin FL-05, no light). The dotted line marked "99.9% killed" indicates a decrease in the CFU/ml by 3 $\log_{10}$ stages; this corresponds to a decrease by 99.9% ("antibacterial action"). N=3; median CFU/ml±SEM.

As apparent from FIGS. 1-4, irradiation of the microorganisms used Staphylococcus aureus (S. aureus) and Escherichia coli (E. coli) at a light dose of 10.5 J/cm² with blue light (390 nm-500 nm) in the absence of a photosensitizer (0 μM of the respective flavin) has no influence on the number of surviving microorganisms in comparison to the unexposed control.

In addition, the results shown in FIGS. 1-4 show that the incubation (10 min or 30 min) of the respective photosensitizer with the microorganisms without subsequent exposure likewise has no influence on the number of surviving microorganisms.

As apparent from FIGS. 1-4, there is a decrease in the CFU/ml and hence inactivation of E. coli and S. aureus after incubation (10 min or 30 min) of the microorganisms as a function of the concentration used of the respective photosensitizers, and subsequent irradiation with a light dose of 10.5 J/cm².

The effectiveness of phototoxicity with respect to bacteria after irradiation was defined according to the following guidelines for hand hygiene in the health sector (Boyce, J. M., and D. Pittet. 2002. Guideline for Hand Hygiene in Health-Care Settings: recommendations of the Healthcare Infection Control Practices Advisory Committee and the HICPAC/SHEA/APIC/IDSA Hand Hygiene Task Force. Infect Control Hosp Epidemiol 23: p. 3-40):

reduction in the CFU/ml by 1 $\log_{10}$ stage ≙ 90% effectiveness reduction in the CFU/ml by 3 $\log_{10}$ stages ≙ 99.9% effectiveness reduction in the CFU/ml by 5 $\log_{10}$ stages ≙ 99.999% effectiveness For effective inactivation, the decrease of ≥3 $\log_{10}$ stages can therefore be adopted, and S. aureus and E. coli were chosen as examples of representatives from the group of the Gram-positive and Gram-negative bacteria (see Boyce J. M and D. Pittet 2009).

The concentration required to achieve a reduction by ≥3 $\log_{10}$ stages is shown in table 1.

TABLE 1

Summary of photodynamic inactivation

| Photosensitizer | Required concentration [μM] to achieve a reduction by ≥3 $\log_{10}$ stages (decrease by 99.9%), irradiation at 10.5 J/cm² | |
|---|---|---|
| | E. coli | S. aureus |
| FL-01 | 10 | 10 |
| FL-03 | >100(*) | 10 |
| FL-04 | >100(*) | 50 |
| FL-05 | >100(*) | 100 |

(*)to date, only a reduction of less than 3 $\log_{10}$ stages has been achieved (99%), at a concentration of 100 μM with subsequent irradiation

What is claimed is:

1. A method for inactivating microorganisms located on or within an object, said method comprising:
   (i) applying upon said object a compound having the formula (1):

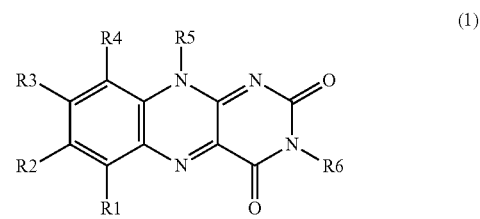

as a photosensitizer in the inactivation of microorganisms, where A) only 1 R1, R2, R3 or R4 radical is an organic radical of the general formula (2), (3) or (4):

where h is an integer from 1 to 20 and k and l are each independently an integer from 0 to 6, where D and E are each independently hydrogen, halogen, hydroxyl, O—R $(^{VIII})$ where $R(^{VIII})$ is methyl, ethyl, n-propyl, n-butyl, phenyl or benzyl, O—C (=O)— where $R(^{IX})$ is hydrogen, methyl, ethyl, n-propyl, n-butyl, phenyl or benzyl, or thiol, and where X is an organic radical having a) only one uncharged, protonatable nitrogen atom, or b) only one positively charged nitrogen atom, and aryl is a substituted or unsubstituted aromatic system having 5 to 20 carbon atoms or a substituted or unsubstituted heteroaromatic system which does not contain any nitrogen atom and has 4 to 20 carbon atoms, and where the radical having the formula (4) is a heteroaromatic system which is bonded to the isoalloxazine ring via a carbon atom of the heteroaromatic system and which contains a) only one uncharged, protonatable nitrogen atom or b) only one positively charged nitrogen atom or where the radical having the formula (4) is formed from compounds having 5 to 7 ring atoms, these compounds being selected from the group consisting of pyrrolidine, pyrrole, oxazole, oxazoline, oxazolidine, isoxazole, isoxazoline, isoxazolidine, thiazole, thiazoline, thiazolidine, isothiazole, isothiazoline, isothiazolidine, piperidine, pyridine, oxazines, dihydrooxazines and tetrahydrooxazines, where the aforementioned compounds are unsubstituted or may be substituted by at least one radical selected from the group consisting of halogen, phenyl, benzyl, straight-chain and branched alkyl having 1 to 20 carbon atoms and hydroxyl, and where the R1, R2, R3 or R4 radicals which are not an organic radical of the general formula (2), (3) or (4) are the same or different and are each independently hydrogen, halogen, hydroxyl, nitro, carboxylate, aldehyde having 1 to 20 carbon atoms, ketone having 2 to 20 carbon atoms, thiol, O-alkyl having 1 to 20 carbon atoms, S-alkyl having 1 to 20 carbon atoms, O-alkenyl having 2 to 20 carbon atoms, S alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having 1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, and where each of the R5 or R6 radicals is the same or different and is independently hydrogen, alkyl having 2 to 20 carbon atoms, alkenyl having 2 to 20 carbon atoms, ether having 2 to 20 carbon atoms, thioester having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, or where B) only 1 R5 or R6 radical is an organic radical of the general formula (2), (3) or (4):

  (2)

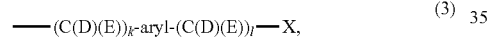  (3)

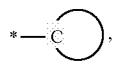  (4)

where h is an integer from 1 to 20 and k and l are each independently an integer from 0 to 6, where D and E are each independently hydrogen, halogen, hydroxyl, O—R $(^{VIII})$ where R$(^{VIII})$ is methyl, ethyl, n-propyl, n-butyl, phenyl or benzyl, O—C(=O)—R$(^{IX})$ where R$(^{IX})$ is hydrogen, methyl, ethyl, n-propyl, n-butyl, phenyl or benzyl, or thiol, and where X is an organic radical having a) only one uncharged, protonatable nitrogen atom, or b) only one positively charged nitrogen atom, and aryl is a substituted or unsubstituted aromatic system having 5 to 20 carbon atoms or a substituted or unsubstituted heteroaromatic system which does not contain any nitrogen atom and has 4 to 20 carbon atoms, and where the radical having the formula (4) is a heteroaromatic system which is bonded to the isoalloxazine ring via a carbon atom of the heteroaromatic system and which contains a) only one uncharged, protonatable nitrogen atom or b) only one positively charged nitrogen atom or where the radical having the formula (4) is formed from compounds having 5 to 7 ring atoms, these compounds being selected from the group consisting of pyrrolidine, pyrrole, oxazole, oxazolidine, isoxazole, isoxazoline, isoxazolidine, thiazole, thiazoline, thiazolidine, isothiazole, isothiazoline, isothiazolidine, piperidine, pyridine, oxazines, dihydrooxazines and tetrahydrooxazines, where the aforementioned compounds are unsubstituted or may be substituted by at least one radical selected from the group consisting of halogen, phenyl, benzyl, straight-chain and branched alkyl having 1 to 20 carbon atoms and hydroxyl, and where the R5 or R6 radical which is not an organic radical of the general formula (2), (3) or (4) is hydrogen, alkyl having 1 to 20 carbon atoms, alkenyl having 2 to 20 carbon atoms, ether having 2 to 20 carbon atoms, thioether having 2 to 20 carbon atoms, cycloalkyl having 3 to 20 carbon atoms, cycloalkenyl having 3 to 20 carbon atoms, aryl having 5 to 20 carbon atoms or heteroaryl which does not contain any nitrogen atom and has 4 to 20 carbon atoms, and where the R1 to R4 radicals are the same or different and are each independently hydrogen, halogen, hydroxyl, thiol, nitro, carboxylate, aldehyde having 1 to 20 carbon atoms, ketone having 1 to 20 carbon atoms, O-alkyl having 1 to 20 carbon atoms, S-alkyl having 1 to 20 carbon atoms, alkenyl having 2 to 20 carbon atoms, S-alkenyl having 2 to 20 carbon atoms, O-aryl having 5 to 20 carbon atoms, S-aryl having 5 to 20 carbon atoms, ether having 2 to 20 carbon atoms, thioether having 2 to 20 carbon atoms, carboxylic ester having ,1 to 20 carbon atoms, carboxamide having 1 to 20 carbon atoms, thioester having 1 to 20 carbon atoms, alkyl having 1 to 20 carbon atoms, alkenyl having 2 to 20 carbon atoms, cycloalkyl having 3 to 20 carbon atoms, cycloalkenyl having 3 to 20 carbon atoms, aryl having 5 to 20 carbon atoms or heteroaryl which does not have any nitrogen atom and has 4 to 20 carbon atoms; and (ii) wherein, following its application, the compound having the formula (I) is irradiated with electromagnetic radiation having a wavelength in a range of from 280 nm to 1000 nm to produce reactive oxygen radicals, singlet oxygen or a combination thereof, and wherein the microorganisms are inactivated or killed by at least one of said reactive oxygen radicals, singlet oxygen and a combination thereof.

2. The method as claimed in claim 1, where X is a radical of formula (5):

  (5)

and where A is an oxygen or sulfur atom and where n is an integer from 1 to 8 and m is an integer from 0 to 100, and where B is a radical of formula (6a), (6b) (7) or (8):

  (6a)

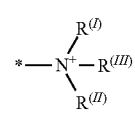  (6b)

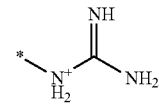  (7)

-continued (8)
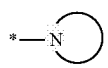

and where each of the R (′) and R(″) radicals is independently selected from hydrogen and C1-C20 alkyl which may be straight-chain or branched, and where R(‴) is hydrogen and where the radical having the formula (8)

(8)
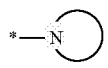

is a substituted or unsubstituted heterocyclic radical having 5 to 7 ring atoms including at least one 1 carbon atom and 1 nitrogen atom and optionally 1 or 2 oxygen or sulfur atoms, where the heterocyclic radical is saturated or unsaturated.

3. The method as claimed in claim 2, where the radical of the formula (4):

(4)
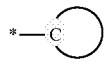

is selected from the group consisting of radicals of formulae (13a), (13b) and (13c):

(13a)
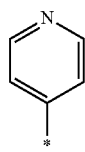

(13b)
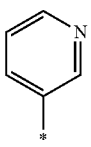

(13c)
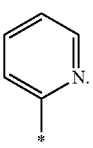

4. The method as claimed in claim 1, where the compound having the formula (1) is selected from compounds having the formulae (14) to (17):

(14)
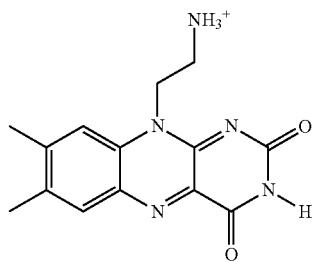

(15)
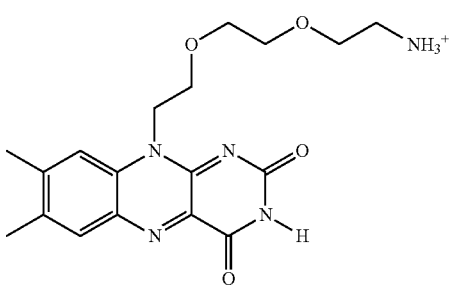

(16)
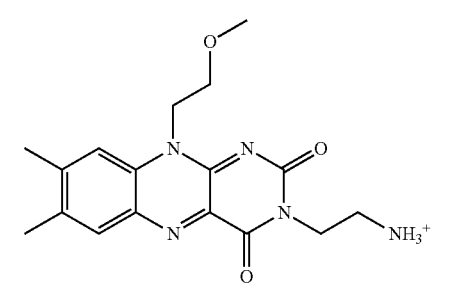

(17)
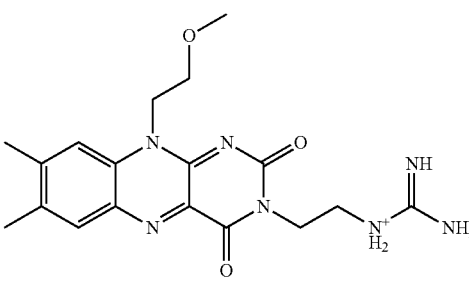

5. The method as claimed in claim 1, where at least one compound of the formula (1) or a pharmacologically acceptable salt and/or ester and/or complex thereof is present in a pharmaceutical composition together with at least one pharmacologically acceptable excipient.

6. The method as claimed in claim 1, where the microorganisms are selected from the group consisting of viruses, archaea, bacteria, bacterial spores, fungi, fungal spores, protozoa, algae and blood-transmissible parasites.

7. The method as claimed in claim 1, wherein said photosensitizer compound is applied to the object during at least one of surface cleaning and coating of said object.

8. The method as claimed in claim 7, wherein the object is selected from the group consisting of medical products, food and drink packaging and hygiene articles.

9. The method as claimed in claim 1, wherein said halogen is selected from the group consisting of chlorine, bromine, iodine and fluorine.

10. The method as claimed in claim 1, wherein the radical having the formula (4) is formed from a compound selected from the group consisting of morpholine, thiazine, azepines, azepane, and thiazepines.

* * * * *